United States Patent
Anderson et al.

(10) Patent No.: US 6,180,343 B1
(45) Date of Patent: Jan. 30, 2001

(54) GREEN FLUORESCENT PROTEIN FUSIONS WITH RANDOM PEPTIDES

(75) Inventors: David Anderson, San Bruno; Jakob Maria Bogenberger, Menlo Park, both of CA (US)

(73) Assignee: Rigel Pharmaceuticals, Inc., S. San Francisco, CA (US)

( * ) Notice: Under 35 U.S.C. 154(b), the term of this patent shall be extended for 0 days.

(21) Appl. No.: 09/169,015

(22) Filed: Oct. 8, 1998

(51) Int. Cl.[7] ............................. C12N 15/63; C12N 15/12
(52) U.S. Cl. .......................... 435/6; 435/320.1; 536/23.4
(58) Field of Search .................... 435/320.1, 6; 536/23.4

(56) References Cited

U.S. PATENT DOCUMENTS 6,025,485    2/2000   Kamb et al. ................... 536/25.32

FOREIGN PATENT DOCUMENTS

| 95/34664 | 12/1995 | (WO) . |
| 97/45538 | 12/1997 | (WO) . |
| 98/36097 | 8/1998  | (WO) . |
| 98/39483 | 9/1998  | (WO) . |
| 99/24617 | 5/1999  | (WO) . |

OTHER PUBLICATIONS

Cepko in Unit 9.9, pp. 9.9.1–9.9.16 in Current Protocols in Molecular Biology, Ausubel et al. Eds. John Wiley & Sons, 1996.*

Borjigin et al., "Insertional Mutagenesis as a Probe of Rhodopsin's Topography, Stability, and Activity," Journal of Biological Chemistry, 269(20):14715–14722 (1994).

Doi et al., "Screening of conformationally constrained random polypeptide libraries displayed on a protein scaffold," CMLS Cellular and Molecular Life Sciences, 54:394–404 (1998).

Hellinga et al., "Construction of New Ligand Binding Sites in Proteins of Known Structure," J. Mol. Biol. 222:787–803 (1991).

Ladner et al., "Constrained peptides as binding entities," TIBTECH, 13:426–430 (1995).

Abedi, M.R. et al., "Green Fluorescent Protein as a Scaffold for Intracellular Presentation of Peptides," *Nucleic Acids Research*, 26(2):623–630, (1998).

* cited by examiner

Primary Examiner—John S. Brusca
(74) Attorney, Agent, or Firm—Flehr Hohbach Test Albritton & Herbert LLP

(57) ABSTRACT

The invention relates to the use of fluorescent proteins, particularly green fluorescent protein (GFP), in fusion constructs with random and defined peptides and peptide libraries, to increase the cellular expression levels, decrease the cellular catabolism, increase the conformational stability relative to linear peptides, and to increase the steady state concentrations of the random peptides and random peptide library members expressed in cells for the purpose of detecting the presence of the peptides and screening random peptide libraries. N-terminal, C-terminal, dual N- and C-terminal and one or more internal fusions are all contemplated. Novel fusions utilizing self-binding peptides to create a conformationally stabilized fusion domain are also contemplated.

21 Claims, 3 Drawing Sheets

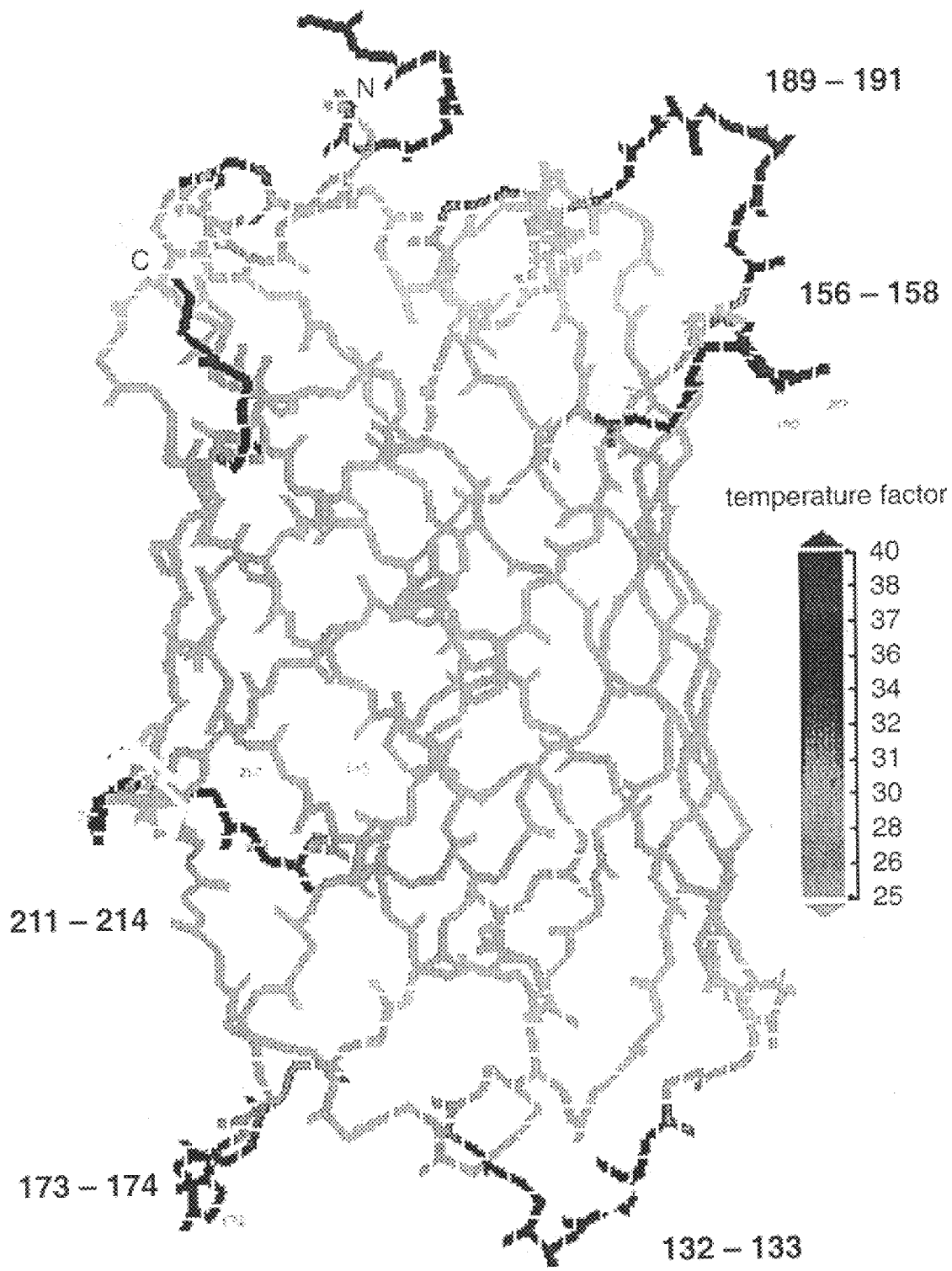
FIG._1

FIG._2A

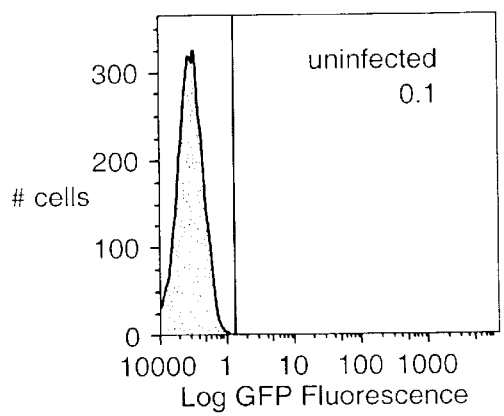
FIG._2B
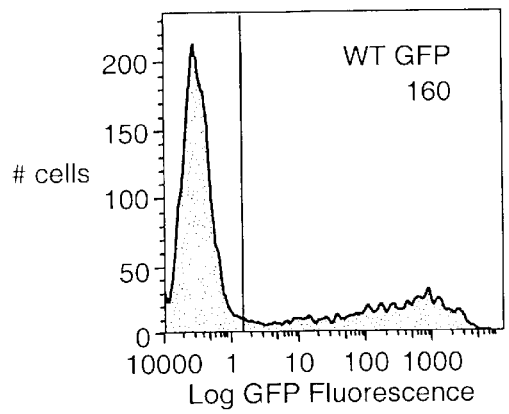
FIG._2C
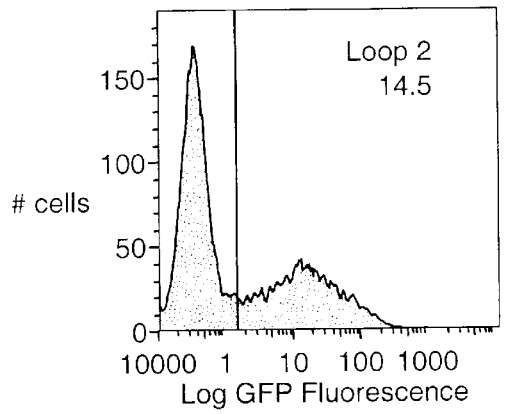
FIG._2D
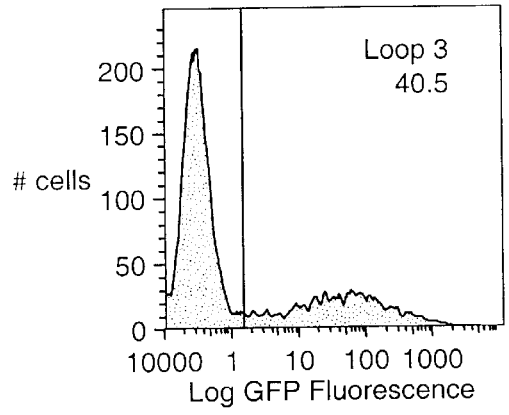
FIG._2E
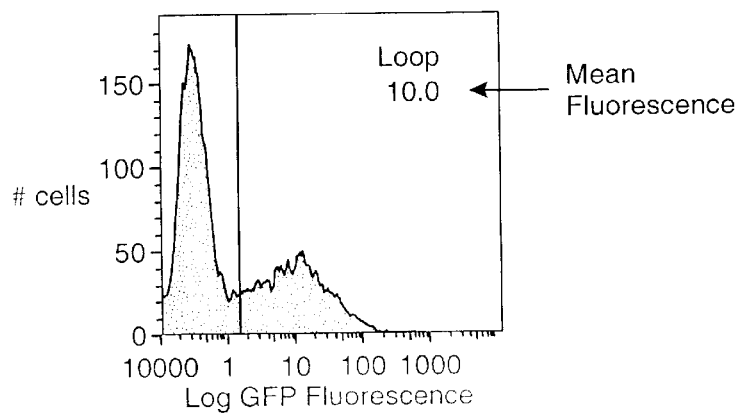
FIG._2F

GREEN FLUORESCENT PROTEIN FUSIONS WITH RANDOM PEPTIDES

FIELD OF THE INVENTION

The invention relates to the use of fluorescent proteins, particularly green fluorescent protein (GFP), in fusion constructs with random and defined peptides and peptide libraries, to increase the cellular expression levels, decrease the cellular catabolism, increase the conformational stability relative to linear peptides, and to increase the steady state concentrations of the random peptides and random peptide library members expressed in cells for the purpose of detecting the presence of the peptides and screening random peptide libraries. N-terminal, C-terminal, dual N- and C-terminal and one or more internal fusions are all contemplated. Novel fusions utilizing self-binding peptides to create a conformationally stabilized fusion domain are also contemplated.

BACKGROUND OF THE INVENTION

The field of biomolecule screening for biologically and therapeutically relevant compounds is rapidly growing. Relevant biomolecules that have been the focus of such screening include chemical libraries, nucleic acid libraries and peptide libraries, in search of molecules that either inhibit or augment the biological activity of identified target molecules. With particular regard to peptide libraries, the isolation of peptide inhibitors of targets and the identification of formal binding partners of targets has been a key focus. However, one particular problem with peptide libraries is the difficulty assessing whether any particular peptide has been expressed, and at what level, prior to determining whether the peptide has a biological effect.

Green fluorescent protein (GFP) is a 238 amino acid protein. The crystal structure of the protein and of several point mutants has been solved (Ormo et al., Science 273, 1392–5, 1996; Yang et al., Nature Biotechnol. 14, 1246–51, 1996). The fluorophore, consisting of a modified tripeptide, is buried inside a relatively rigid beta-can structure, where it is almost completely protected from solvent access. The fluorescence of this protein is sensitive to a number of point mutations (Phillips, G. N., Curr. Opin. Struct. Biol. 7, 821–27,1997). The fluorescence appears to be a sensitive indication of the preservation of the native structure of the protein, since any disruption of the structure allowing solvent access to the fluorophoric tripeptide will quench the fluorescence.

Abedi et al (Nucleic Acids Res. 26, 623–30, 1998) have inserted peptides between residues contained in several GFP loops. Inserts of the short sequence LEEFGS (SEQ ID NO: 1) between adjacent residues at 10 internal insertion sites were tried. Of these, inserts at three sites, between residues 157–158, 172–173 and 194–195 gave fluorescence of at least 1% of that of wild type GFP. Only inserts between residues 157–158 and 172–173 had fluorescence of at least 10% of wild type GFP. When -SAG-random 20mer-GAS- peptide sequences were inserted at different sites internal to GFP, only two sites gave mean fluorescence intensities of 2% or more of the GFP-random peptide sequences 10-fold above background fluorescence. These sites were insertions between residues 157–158 and 172–173.

It is an object of the invention to provide compositions of fusion constructs of peptides with fluorescent proteins such as GFP, and methods of using such constructs in screening of peptide libraries.

SUMMARY OF THE INVENTION

In accordance with the objects outlined above, the present invention provides fusion proteins comprising a random peptide fused to green fluorescent protein (GFP). Preferred embodiments utilize fusions to the N- and C-termini of GFP comprising presentation structures capable of presenting the peptide in a conformationally restricted form. Further preferred embodiments fuse the random peptide to an internal position of GFP, including the loops comprising amino acids 130 to 135, amino acids 154 to 159, amino acids 172 to 175, amino acids 188 to 193, and amino acids 208 to 216.

In a further aspect, the invention provides fusion nucleic acids encoding the fusion proteins.

In an additional aspect, the present invention provides libraries of: a) fusion proteins; b) fusion nucleic acids; c) expression vectors comprising the fusion nucleic acids; and d) host cells comprising the fusion nucleic acids.

In a further aspect, the invention provides methods of screening for bioactive peptides confering a particular phenotype. The methods comprise providing cells containing a fusion nucleic acid comprising nucleic acid encoding a fusion protein comprising GFP and a random peptide as above. The cells are subjected to conditions wherein the fusion protein is expressed. The cells are then assayed for the phenotype.

BRIEF DESCRIPTION OF THE DRAWINGS

FIG. 1 depicts the crystal structure of GFP showing the temperature factors used to pick some of the loops for internal insertion of random peptides.

FIGS. 2A, 2B, 2C, 2D, 2E and 2F (SEQ ID NO: 2) depict the results of the examples. FIG. 2A schematically depicts the location of the loops. FIGS. 2B–2F show the results and the mean fluorescence.

DETAILED DESCRIPTION OF THE INVENTION

Screening of combinatorial libraries of potential drugs on therapeutically relevant target cells is a rapidly growing and important field. Peptide libraries are an important subset of these libraries. However, to facilitate intracellular screening of these peptide libraries, a number of hurdles must be overcome. In order to express and subsequently screen functional peptides in cells, the peptides need to be expressed in sufficient quantities to overcome catabolic mechanisms such as proteolysis and transport out of the cytoplasm into endosomes. The peptides also should be conformationally stabilized relative to linear peptides to allow a higher binding affinity for their cellular targets. In addition, measuring the expression level of these peptides can be difficult. Furthermore, it is generally difficult to follow the expression of peptides in specific cells, to ascertain whether any particular cell is expressing a member of the library. To overcome these problems, the present invention is directed to fusions of green fluorescent protein (GFP), including variants, and random peptides that are fused in such a manner that the structure of the GFP is not significantly perturbed and the peptide is metabolically conformationally stabilized. This allows the creation of a peptide library that is easily monitored, both for its presence within cells and its quantity.

Accordingly, the present invention provides fusions of green fluorescent protein (GFP) and random peptides. By "green fluorescent protein" or "GFP" herein is meant a protein with at least 30% sequence identity to GFP and exhibits fluorescence at 490 to 600 nm. The wild-type GFP is 238 amino acids in length, contains a modified tripeptide fluorophore buried inside a relatively rigid β-can structure which protects the fluorophore from the solvent, and thus solvent quenching. See Prasher et al., Gene 111(2):229–233 (1992); Cody et al., Biochem. 32(5):1212–1218 (1993); Ormo et al, Science 273:1392–1395 (1996); and Yang et al., Nat. Biotech. 14:1246–1251 (1996), all of which are hereby incorporated by reference in their entirety). Included within the definition of GFP are derivatives of GFP, including amino acid substitutions, insertions and deletions. See for example WO 98/06737 and U.S. Pat. No. 5,777,079, both of which are hereby incorporated by reference in their entirety. Accordingly, the GFP proteins utilized in the present invention may be shorter or longer than the wild type sequence. Thus, in a preferred embodiment, included within the definition of GFP proteins are portions or fragments of the wild type sequence. For example, GFP deletion mutants can be made. At the N-terminus, it is known that only the first amino acid of the protein may be deleted without loss of fluorescence. At the C-terminus, up to 7 residues can be deleted without loss of fluorescence; see Phillips et al., Current Opin. Structural Biol. 7:821 (1997)).

In one embodiment, the GFP proteins are derivative or variant GFP proteins. That is, as outlined more fully below, the derivative GFP will contain at least one amino acid substitution, deletion or insertion, with amino acid substitutions being particularly preferred. The amino acid substitution, insertion or deletion may occur at any residue within the GFP protein. These variants ordinarily are prepared by site specific mutagenesis of nucleotides in the DNA encoding the GFP protein, using cassette or PCR mutagenesis or other techniques well known in the art, to produce DNA encoding the variant, and thereafter expressing the DNA in recombinant cell culture as outlined above. However, variant GFP protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the GFP protein amino acid sequence. The variants typically exhibit the same qualitative biological activity as the naturally occurring analogue, although variants can also be selected which have modified characteristics as will be more fully outlined below. That is, in a preferred embodiment, when non-wild-type GFP is used, the derivative preferably has at least 1% of wild-type fluorescence, with at least about 10% being preferred, at least about 50–60% being particularly preferred and 95% to 98% to 100% being especially preferred. In general, what is important is that there is enough fluorescence to allow sorting and/or detection above background, for example using a fluorescence-activated cell sorter (FACS) machine. However, in some embodiments, it is possible to detect the fusion proteins non-fluorescently, using, for example, antibodies directed to either an epitope tag (i.e. purification sequence) or to the GFP itself. In this case the GFP scaffold does not have to be fluorescent.

While the site or region for introducing an amino acid sequence variation is predetermined, the mutation per se need not be predetermined. For example, in order to optimize the performance of a mutation at a given site, random mutagenesis may be conducted at the target codon or region and the expressed GFP variants screened for the optimal combination of desired activity. Techniques for making substitution mutations at predetermined sites in DNA having a known sequence are well known, for example, M13 primer mutagenesis and PCR mutagenesis. Screening of the mutants is done using assays of GFP protein activities, i.e. fluorescence.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the GFP protein are desired, substitutions are generally made in accordance with the following chart:

CHART I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

As outlined above, the variants typically exhibit the same qualitative biological activity (i.e. fluorescence) although variants also are selected to modify the characteristics of the GFP proteins as needed.

In addition, GFP proteins can be made that are longer than the wild-type, for example, by the addition of epitope or purification tags, the addition of other fusion sequences, etc., as is more fully outlined below.

The GFP is fused to a random peptide to form a fusion polypeptide. By "fused" or "operably linked" herein is meant that the random peptide, as defined below, and the GFP, are linked together, in such a manner as to minimize the disruption to the stability of the GFP structure (i.e. it can retain fluorescence, as outlined herein) or maintains a Tm of at least 42° C. As outlined below, the fusion polypeptide (or fusion polynucleotide encoding the fusion polypeptide) can comprise further components as well, including multiple peptides at multiple loops.

The peptides (and nucleic acids encoding them) are randomized, either fully randomized or they are biased in their randomization, e.g. in nucleotide/residue frequency generally or per position. By "randomized" or grammatical equivalents herein is meant that each nucleic acid and peptide consists of essentially random nucleotides and amino acids, respectively. As is more fully described below, the nucleic acids which give rise to the peptides are chemically synthesized, and thus may incorporate any nucleotide at any position. Thus, when the nucleic acids are expressed to form peptides, any amino acid residue may be incorporated at any position. The synthetic process can be designed to generate randomized nucleic acids, to allow the formation of all or most of the possible combinations over the length of the nucleic acid, thus forming a library of randomized nucleic acids.

The library should provide a sufficiently structurally diverse population of randomized expression products to effect a probabilistically sufficient range of cellular responses to provide one or more cells exhibiting a desired response. Accordingly, an interaction library must be large enough so that at least one of its members will have a structure that gives it affinity for some molecule, protein, or other factor whose activity is necessary for completion of the signaling pathway. Although it is difficult to gauge the required absolute size of an interaction library, nature provides a hint with the immune response: a diversity of $10^7$–$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide 7 to 20 amino acids in length, such as proposed here for expression in retroviruses, has the potential to code for $20^7$ ($10^9$) to $20^{20}$. Thus, for example, with libraries of $10^7$ to $10^8$ per ml of retroviral particles the present methods allow a "working" subset of a theoretically complete interaction library for 7 amino acids, and a subset of shapes for the $20^{20}$ library. Thus, in a preferred embodiment, at least $10^6$, preferably at least $10^6$, more preferably at least $10^7$, still more preferably at least $10^8$ and most preferably at least $10^9$ different peptides may be simultaneously analyzed as outlined herein.

It is important to understand that in any library system encoded by oligonucleotide synthesis one cannot have complete control over the codons that will eventually be incorporated into the peptide structure. This is especially true in the case of codons encoding stop signals (TAA, TGA, TAG). In a synthesis with NNN as the random region, there is a 3/64, or 4.69%, chance that the codon will be a stop codon. Thus, in a peptide of 10 residues, there is an unacceptable high likelihood that 46.7% of the peptides will prematurely terminate. For free peptide structures this is perhaps not a problem. But for larger structures, such as those envisioned here, such termination will lead to sterile peptide expression. To alleviate this, random residues are encoded as NNK, where K=T or G. This allows for encoding of all potential amino acids (changing their relative representation slightly), but importantly preventing the encoding of two stop residues TAA and TGA. Thus, libraries encoding a 10 amino acid peptide will have a 15.6% chance to terminate prematurely. However, it should be noted that the present invention allows screening of libraries containing terminated peptides in a loop, since the GFP will not fluoresce and thus these peptides will not be selected.

In a preferred embodiment, the peptide library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

For example, individual residues may be fixed in the random peptide sequence of the insert to create a structural bias, similar to the concept of presentation structures outlined below. A preferred embodiment utilizes inserts of a general structure -gly$_{2-8}$-aa$_1$-aa$_2$- . . . -aa$_n$-gly$_{2-8}$- where the random insert sequence is aa$_1$ to aa$_n$. This sequence can be constrained by fixing one or more of the n residues as prolines (which will significantly restrict the conformation space of the entire loop), as bulky amino acids such as W, R, K, L, I, V, F, or Y, or biasing the set of random amino acids to include only bulky residues such as E, F, H, I, K, L, M, Q, R, T, V, W, and Y. Due to the larger size of the side chains, these residues will have fewer ways to pack into a small space that is defined by that available to a loop, and thus there will be fewer available loop conformations.

In an alternative embodiment, the random libraries can be biased to a particular secondary structure by including an appropriate number of residues (beyond the glycine linkers) which prefer the particular secondary structure. For example, to create an alpha-helical bias the entire loop insert might look like -gly$_{2-8}$-helix former $_{4-8}$-random residues-helix former $_{4-8}$-gly$_{2-8}$-, where the 4–8 helix formers at each end of the randomized region will nucleate an alpha helix and raise the probability that the random inserts will be helical; to further this bias, the randomized region can be devoid of strong helix breakers such as pro and gly; examples of strong helix forming residues would include M, A, K, L, D, E, R, Q, F, I and V In a preferred embodiment, the bias is towards peptides that interact with known classes of molecules. For example, it is known that much of intracellular signaling is carried out via short regions of polypeptides interacting with other polypeptides through small peptide domains. For instance, a short region from the HIV-1 envelope cytoplasmic domain has been previously shown to block the action of cellular calmodulin. Regions of the Fas cytoplasmic domain, which shows homology to the mastoparan toxin from Wasps, can be limited to a short peptide region with death-inducing apoptotic or G protein inducing functions. Magainin, a natural peptide derived from Xenopus, can have potent anti-tumour and anti-microbial activity. Short peptide fragments of a protein kinase C isozyme (βPKC), have been shown to block nuclear translocation of βPKC in Xenopus oocytes following stimulation. And, short SH-3 target peptides have been used as psuedosubstrates for specific binding to SH-3 proteins. This is of course a short list of available peptides with biological activity, as the literature is dense in this area. Thus, there is much precedent for the potential of small peptides to have activity on intracellular signaling cascades. In addition, agonists and antagonists of any number of molecules may be used as the basis of biased randomization of peptides as well.

Thus, a number of molecules or protein domains are suitable as starting points for the generation of biased randomized peptides. A large number of small molecule domains are known, that confer a common function, structure or affinity. In addition, as is appreciated in the art, areas of weak amino acid homology may have strong structural homology. A number of these molecules, domains, and/or corresponding consensus sequences, are known, including, but are not limited to, SH-2 domains, SH-3 domains, Pleckstrin, death domains, protease cleavage/recognition sites, enzyme inhibitors, enzyme substrates, Traf, etc. Similarly, there are a number of known nucleic acid binding proteins containing domains suitable for use in the invention. For example, leucine zipper consensus sequences are known.

Generally, at least 4, preferably at least 10, more preferably at least 15 amino acid positions need to be randomized; again, more are preferable if the randomization is less than perfect.

In a preferred embodiment, biased SH-3 domain-binding oligonucleotides/peptides are made. SH-3 domains have been shown to recognize short target motifs (SH-3 domain-binding peptides), about ten to twelve residues in a linear sequence, that can be encoded as short peptides with high affinity for the target SH-3 domain. Consensus sequences for SH-3 domain binding proteins have been proposed. Thus, in a preferred embodiment, oligos/peptides are made with the following biases 1. XXXPPXPXX (SEQ ID NO:3), wherein X is a randomized residue.
2. (within the positions of residue positions 11 to −2):

```
        11  10   9    8    7    6    5    4    3    2    1
Met Glyaa11aa10 aa9  aa8  aa7  Arg  Pro  Leu  Pro  Pro  hyd
     0  -1  -2
Pro hyd hyd Gly Gly Pro Pro STOP                                    (SEQ ID NO:55)
atg ggc nnk nnk nnk nnk nnk aga cct ctg cct cca sbk ggg cct sbk sbk gga
ggc cca cct TAA1.                                                   (SEQ ID NO:54)
```

In this embodiment, the N-terminus flanking region is suggested to have the greatest effects on binding affinity and is therefore entirely randomized. "Hyd" indicates a bias toward a hydrophobic residue, i.e.—Val, Ala, Gly, Leu, Pro, Arg. To encode a hydrophobically biased residue, "sbk" codon biased structure is used. Examination of the codons within the genetic code will ensure this encodes generally hydrophobic residues. s=g,c; b=t, g, c; v=a, g, c; m=a, c; k=t, g; n=a, t, g, c.

In general, the random peptides range from about 4 to about 50 residues in length, with from about 5 to about 30 being preferred, and from about 10 to about 20 being especially preferred.

The random peptide(s) can be fused to the GFP in a variety of positions, as is more fully outlined below, to form fusion polypeptides. The fusion polypeptide preferably includes additional components, including, but not limited to, fusion partners and linkers.

By "fusion partner" herein is meant a sequence that is associated with the random peptide that confers upon all members of the library in that class a common function or ability. Fusion partners can be heterologous (i.e. not native to the host cell), or synthetic (not native to any cell). Suitable fusion partners include, but are not limited to: a) presentation structures, as defined below, which provide the peptides in a conformationally restricted or stable form; b) targeting sequences, defined below, which allow the localization of the peptide into a subcellular or extracellular compartment; c) rescue sequences as defined below, which allow the purification or isolation of either the peptides or the nucleic acids encoding them; d) stability sequences, which confer stability or protection from degradation to the peptide or the nucleic acid encoding it, for example resistance to proteolytic degradation; e) linker sequences, which conformationally decouple the random peptide elements from the GFP itself, which keep the peptide from interfering with GFP folding; or f), any combination of a), b), c), d) and e) as well as linker sequences as needed.

In a preferred embodiment, the fusion partner is a presentation structure. By "presentation structure" or grammatical equivalents herein is meant a sequence, which, when fused to peptides, causes the peptides to assume a conformationally restricted form. Proteins interact with each other largely through conformationally constrained domains. Although small peptides with freely rotating amino and carboxyl termini can have potent functions as is known in the art, the conversion of such peptide structures into pharmacologic agents is difficult due to the inability to predict side-chain positions for peptidomimetic synthesis. Therefore the presentation of peptides in conformationally constrained structures will benefit both the later generation of pharmacophore models and pharmaceuticals and will also likely lead to higher affinity interactions of the peptide with the target protein. This fact has been recognized in the combinatorial library generation systems using biologically generated short peptides in bacterial phage systems. A number of workers have constructed small domain molecules in which one might present randomized peptide structures.

Thus, synthetic presentation structures, i.e. artificial polypeptides, are capable of presenting a randomized peptide as a conformationally-restricted domain. Generally such presentation structures comprise a first portion joined to the N-terminal end of the randomized peptide, and a second portion joined to the C-terminal end of the peptide; that is, the peptide is inserted into the presentation structure, although variations may be made, as outlined below, in which elements of the presentation structure are included within the random peptide sequence. To increase the functional isolation of the randomized expression product, the presentation structures are selected or designed to have minimal biologically activity when expressed in the target cell.

Preferred presentation structures maximize accessibility to the peptide by presenting it on an exterior surface such as a loop, and also cause further conformational constraints in a peptide. Accordingly, suitable presentation structures include, but are not limited to, dimerization sequences, minibody structures, loops on beta turns and coiled-coil stem structures in which residues not critical to structure are randomized, zinc-finger domains, cysteine-linked (disulfide) structures, transglutaminase linked structures, cyclic peptides, B-loop structures, helical barrels or bundles, leucine zipper motifs, etc.

In a preferred embodiment, the presentation structure is a coiled-coil structure, allowing the presentation of the randomized peptide on an exterior loop. See, for example, Myszka et al., Biochem. 33:2362–2373 (1994), hereby incorporated by reference). Using this system investigators have isolated peptides capable of high affinity interaction with the appropriate target. In general, coiled-coil structures allow for between 6 to 20 randomized positions.

A preferred coiled-coil presentation structure is as follows:
MGC<u>AALESEVSALESEVAS<u>LE</u>SEVAAL</u>GRGDMP <u>LAAVKSK<u>L</u>SAVKSKLASVK<u>SK</u>LAA</u>CGPP (SEQ ID NO: 4) The underlined regions represent a coiled-coil leucine zipper region defined previously (see Martin et al., EMBO J. 13(22):5303–5309 (1994), incorporated by reference). The bolded GRGDMP (SEQ ID NO: 5) region represents the loop structure and when appropriately replaced with randomized peptides (i.e. peptides, generally depicted herein as $(X)_n$, where X is an amino acid residue and n is an integer of at least 5 or 6) can be of variable length. The replacement of the bolded region is facilitated by encoding restriction endonuclease sites in the underlined regions, which allows the direct incorporation of randomized oligonucleotides at these positions. For example, a preferred embodiment generates a XhoI site at the double underlined LE site and a HindIII site at the double-underlined KL site.

In a preferred embodiment, the presentation structure is a minibody structure. A "minibody" is essentially composed of a minimal antibody complementarity region. The minibody presentation structure generally provides two randomizing regions that in the folded protein are presented along a single face of the tertiary structure. See for example Bianchi et al., J. Mol. Biol. 236(2):649–59 (1994), and references cited therein, all of which are incorporated by reference). Investigators have shown this minimal domain is stable in solution and have used phage selection systems in combinatorial libraries to select minibodies with peptide regions exhibiting high affinity, $Kd=10^{-7}$, for the pro-inflammatory cytokine IL-6.

A preferred minibody presentation structure is as follows:
MGRNSQATSGFT/FSHFYMEWVRGGEYIAASR HKHNKYTTEYSASVKGRYIVSRDTSQSILYLQ KKKGPP (SEQ ID NO: 6). The bold, underline regions are the regions which may be randomized. The italized phenylalanine must be invariant in the first randomizing region. The entire peptide is cloned in a three-oligonucleotide variation of the coiled-coil embodiment, thus allowing two different randomizing regions to be incorporated simultaneously. This embodiment utilizes non-palindromic BstXI sites on the termini.

In a preferred embodiment, the presentation structure is a sequence that contains generally two cysteine residues, such that a disulfide bond may be formed, resulting in a conformationally constrained sequence. This embodiment is particularly preferred ex vivo, for example when secretory targeting sequences are used. As will be appreciated by those in the art, any number of random sequences, with or without spacer or linking sequences, may be flanked with cysteine residues. In other embodiments, effective presentation structures may be generated by the random regions themselves. For example, the random regions may be "doped" with cysteine residues which, under the appropriate redox conditions, may result in highly crosslinked structured conformations, similar to a presentation structure. Similarly, the randomization regions may be controlled to contain a certain number of residues to confer β-sheet or α-helical structures.

In a preferred embodiment, the presentation sequence confers the ability to bind metal ions to confer secondary structure. Thus, for example, C2H2 zinc finger sequences are used; C2H2 sequences have two cysteines and two histidines placed such that a zinc ion is chelated. Zinc finger domains are known to occur independently in multiple zinc-finger peptides to form structurally independent, flexibly linked domains. See J. Mol. Biol. 228:619 (1992). A general consensus sequence is (5 amino acids)-C-(2 to 3 amino acids)-C-(4 to 12 amino acids)-H-(3 amino acids)-H-(5 amino acids). A preferred example would be -FQCEEC (SEQ ID NO:7) random peptide of 3 to 20 amino acids-HIRSHTG (SEQ ID NO:8)-.

Similarly, CCHC boxes can be used (see Biochem. Biophys. Res. Commun. 242:385 (1998)), that have a consensus seqeunce -C-(2 amino acids)-C-(4 to 20 random peptide)-H-(4 amino acids)-C- (see Bavoso et al., Biochem. Biophys. Res. Comm. 242(2):385 (1998), hereby incorporated by reference. Preferred examples include (1) -VKCFNC (SEQ ID NO:9)- 4 to 20 random amino acids-HTARNCR (SEQ ID NO: 10)-, based on the nucleocapsid protein P2; (2) a sequence modified from that of the naturally occuring zinc-binding peptide of the Lasp-1 LIM domain (Hammarstrom et al., Biochem. 35:12723 (1996)); and (3) -MNPNCARCG (SEQ ID NO:11)- 4 to 20 random amino acids-HKACF (SEQ ID NO: 12)-, based on the nmr structural ensemble 1ZFP (Hammarstrom et al., Biochem. 35 U.S.C. 35(39): 12723 (1996).

In a preferred embodiment, the presentation structure is a dimerization sequence, including self-binding peptides. A dimerization sequence allows the non-covalent association of two peptide sequences, which can be the same or different, with sufficient affinity to remain associated under normal physiological conditions. These sequences may be used in several ways. In a preferred embodiment, one terminus of the random peptide is joined to a first dimerization sequence and the other terminus is joined to a second dimerization sequence, which can be the same or different from the first sequence. This allows the formation of a loop upon association of the dimerizing sequences. Alternatively, the use of these sequences effectively allows small libraries of random peptides (for example, $10^4$) to become large libraries if two peptides per cell are generated which then dimerize, to form an effective library of $10^8$ ($10^4 \times 10^4$). It also allows the formation of longer random peptides, if needed, or more structurally complex random peptide molecules. The dimers may be homo- or heterodimers.

Dimerization sequences may be a single sequence that self-aggregates, or two different sequences that associate. That is, nucleic acids encoding both a first random peptide with dimerization sequence 1, and a second random peptide with dimerization sequence 2, such that upon introduction into a cell and expression of the nucleic acid, dimerization sequence 1 associates with dimerization sequence 2 to form a new random peptide structure. The use of dimerization sequences allows the "circularization" of the random peptides; that is, if a dimerization sequence is used at each terminus of the peptide, the resulting structure can form a "stem-loop" type of structure. Furthermore, the use of dimerizing sequences fused to both the N- and C-terminus of the GFP forms a noncovalently cyclized GFP random peptide library.

Suitable dimerization sequences will encompass a wide variety of sequences. Any number of protein-protein interaction sites are known. In addition, dimerization sequences may also be elucidated using standard methods such as the yeast two hybrid system, traditional biochemical affinity binding studies, or even using the present methods. See U.S. Ser. No. 60/080,444, filed Apr. 2, 1998, hereby incorporated by reference in its entireity. Particularly preferred dimerization peptide sequences include, but are not limited to, -EFLIVKS (SEQ ID NO:13)-, EEFLIVKKS (SEQ ID NO:14)-, -FESIKLV (SEQ ID NO:15)-, and -VSIKFEL (SEQ ID NO:16)-.

In a preferred embodiment, the fusion partner is a targeting sequence. As will be appreciated by those in the art, the localization of proteins within a cell is a simple method for increasing effective concentration and determining function. For example, RAF1 when localized to the mitochondrial membrane can inhibit the anti-apoptotic effect of BCL-2. Similarly, membrane bound Sos induces Ras mediated signaling in T-lymphocytes. These mechanisms are thought to rely on the principle of limiting the search space for ligands, that is to say, the localization of a protein to the plasma membrane limits the search for its ligand to that limited dimensional space near the membrane as opposed to the three dimensional space of the cytoplasm. Alternatively, the concentration of a protein can also be simply increased by nature of the localization. Shuttling the proteins into the nucleus confines them to a smaller space thereby increasing concentration. Finally, the ligand or target may simply be localized to a specific compartment, and inhibitors must be localized appropriately.

Thus, suitable targeting sequences include, but are not limited to, binding sequences capable of causing binding of the expression product to a predetermined molecule or class of molecules while retaining bioactivity of the expression product, (for example by using enzyme inhibitor or substrate sequences to target a class of relevant enzymes); sequences signalling selective degradation, of itself or co-bound proteins; and signal sequences capable of constitutively localizing the peptides to a predetermined cellular locale, including a) subcellular locations such as the Golgi, endoplasmic reticulum, nucleus, nucleoli, nuclear membrane, mitochondria, chloroplast, secretory vesicles, lysosome, and cellular membrane; and b) extracellular locations via a secretory signal. Particularly preferred is localization to either subcellular locations or to the outside of the cell via secretion.

In a preferred embodiment, the targeting sequence is a nuclear localization signal (NLS). NLSs are generally short, positively charged (basic) domains that serve to direct the entire protein in which they occur to the cell's nucleus. Numerous NLS amino acid sequences have been reported including single basic NLS's such as that of the SV40 (monkey virus) large T Antigen (Pro Lys Lys Lys Arg Lys Val (SEQ ID NO: 17)), Kalderon (1984), et al., Cell, 39:499–509; the human retinoic acid receptor-β nuclear localization signal (ARRRRP (SEQ ID NO: 18)); NFκB p50 (EEVQRKRQKL (SEQ ID NO: 19); Ghosh et al., Cell 62:1019 (1990); NFκB p65 (EEKRKRTYE (SEQ ID NO: 20); Nolan et al., Cell 64:961 (1991); and others (see for example Boulikas, J. Cell. Biochem. 55(1):32–58 (1994), hereby incorporated by reference) and double basic NLS's exemplified by that of the Xenopus (African clawed toad) protein, nucleoplasmin (Ala Val Lys Arg Pro Ala Ala Thr Lys Lys Ala Gly Gln Ala Lys Lys Lys Lys Leu Asp (SEQ ID NO: 21)), Dingwall, et al., Cell, 30:449–458, 1982 and Dingwall, et al., J. Cell Biol., 107:641–849; 1988). Numerous localization studies have demonstrated that NLSs incorporated in synthetic peptides or grafted onto reporter proteins not normally targeted to the cell nucleus cause these peptides and reporter proteins to be concentrated in the nucleus. See, for example, Dingwall, and Laskey, Ann, Rev. Cell Biol., 2:367–390, 1986; Bonnerot, et al., Proc. Natl. Acad. Sci. U.S.A.,84:6795–6799, 1987; Galileo, et al., Proc. Natl. Acad. Sci. U.S.A., 87:458–462, 1990.

In a preferred embodiment, the targeting sequence is a membrane anchoring signal sequence. This is particularly useful since many parasites and pathogens bind to the membrane, in addition to the fact that many intracellular events originate at the plasma membrane. Thus, membrane-bound peptide libraries are useful for both the identification of important elements in these processes as well as for the discovery of effective inhibitors. The invention provides methods for presenting the randomized expression product extracellularly or in the cytoplasmic space. For extracellular presentation, a membrane anchoring region is provided at the carboxyl terminus of the peptide presentation structure. The randomized expression product region is expressed on the cell surface and presented to the extracellular space, such that it can bind to other surface molecules (affecting their function) or molecules present in the extracellular medium. The binding of such molecules could confer function on the cells expressing a peptide that binds the molecule. The cytoplasmic region could be neutral or could contain a domain that, when the extracellular randomized expression product region is bound, confers a function on the cells (activation of a kinase, phosphatase, binding of other cellular components to effect function). Similarly, the randomized expression product-containing region could be contained within a cytoplasmic region, and the transmembrane region and extracellular region remain constant or have a defined function.

Membrane-anchoring sequences are well known in the art and are based on the genetic geometry of mammalian transmembrane molecules. Peptides are inserted into the membrane based on a signal sequence (designated herein as ssTM) and require a hydrophobic transmembrane domain (herein TM). The transmembrane proteins are inserted into the membrane such that the regions encoded 5' of the transmembrane domain are extracellular and the sequences 3' become intracellular. Of course, if these transmembrane domains are placed 5' of the variable region, they will serve to anchor it as an intracellular domain, which may be desirable in some embodiments. ssTMs and TMs are known for a wide variety of membrane bound proteins, and these sequences may be used accordingly, either as pairs from a particular protein or with each component being taken from a different protein, or alternatively, the sequences may be synthetic, and derived entirely from consensus as artificial delivery domains.

As will be appreciated by those in the art, membrane-anchoring sequences, including both ssTM and TM, are known for a wide variety of proteins and any of these may be used. Particularly preferred membrane-anchoring sequences include, but are not limited to, those derived from CD8, ICAM-2, IL-8R, CD4 and LFA-1.

Useful sequences include sequences from: 1) class I integral membrane proteins such as IL-2 receptor beta-chain (residues 1–26 are the signal sequence, 241–265 are the transmembrane residues; see Hatakeyama et al., Science 244:551 (1989) and von Heijne et al, Eur. J. Biochem. 174:671 (1988)) and insulin receptor beta chain (residues 1–27 are the signal, 957–959 are the transmembrane domain and 960–1382 are the cytoplasmic domain; see Hatakeyama, supra, and Ebina et al., Cell 40:747 (1985)); 2) class II integral membrane proteins such as neutral endopeptidase (residues 29–51 are the transmembrane domain, 2–28 are the cytoplasmic domain; see Malfroy et al., Biochem. Biophys. Res. Commun. 144:59 (1987)); 3) type III proteins such as human cytochrome P450 NF25 (Hatakeyama, supra); and 4) type IV proteins such as human P-glycoprotein (Hatakeyama, supra). Particularly preferred are CD8 and ICAM-2. For example, the signal sequences from CD8 and ICAM-2 lie at the extreme 5' end of the transcript. These consist of the amino acids 1–32 in the case of CD8 (MASPLTRFLSLNLLLLGESILGSGEAKPQAP (SEQ ID NO: 22); Nakauchi et al., PNAS U.S.A. 82:5126 (1985) and 1–21 in the case of ICAM-2 (MSSFGYRTLTVALFTLICCPG (SEQ ID NO: 23); Staunton et al., Nature (London) 339:61 (1989)). These leader sequences deliver the construct to the membrane while the hydrophobic transmembrane domains, placed 3' of the random peptide region, serve to anchor the construct in the membrane. These transmembrane domains are encompassed by amino acids 145–195 from CD8 (PQRPEDCRPRGSVKGTGLDFACDIYIWAPLAGICVA LLLSLIITLICYHSR (SEQ ID NO: 24); Nakauchi, supra) and 224–256 from ICAM-2 (MVIIVTVVSVLLSLFVTSVLLCFIFGQHLRQQR (SEQ ID NO: 25); Staunton, supra).

Alternatively, membrane anchoring sequences include the GPI anchor, which results in a covalent bond between the molecule and the lipid bilayer via a glycosyl-phosphatidylinositol bond for example in DAF (PNKGSGTTSGTTRLLSGHTCFTLTGLLGTLVTMGLLT (SEQ ID NO: 26), with the bolded serine the site of the anchor; see Homans et al., Nature 333(6170):269–72 (1988), and Moran et al., J. Biol. Chem. 266:1250 (1991)). In order to do this, the GPI sequence from Thy-1 can be cassetted 3' of the variable region in place of a transmembrane sequence.

Similarly, myristylation sequences can serve as membrane anchoring sequences. It is known that the myristylation of c-src recruits it to the plasma membrane. This is a simple and effective method of membrane localization, given that the first 14 amino acids of the protein are solely responsible for this function: MGSSKSKPKDPSQR (SEQ ID NO: 27) (see Cross et al., Mol. Cell. Biol. 4(9):1834 (1984); Spencer et al., Science 262:1019–1024 (1993), both of which are hereby incorporated by reference). This motif has already been shown to be effective in the localization of reporter genes and can be used to anchor the zeta chain of the TCR. This motif is placed 5' of the variable region in order to localize the construct to the plasma membrane. Other modifications such as palmitoylation can be used to anchor constructs in the plasma membrane; for example, palmitoylation sequences from the G protein-coupled receptor kinase GRK6 sequence (LLQRLFSRQDCCGNCSDSEEELPTRL (SEQ ID NO: 28), with the bold cysteines being palmitolyated; Stoffel et al., J. Biol. Chem 269:27791 (1994)); from rhodopsin (KQFRNCMLTSLCCGKNPLGD (SEQ ID NO: 29); Barnstable et al., J. Mol. Neurosci. 5(3):207 (1994)); and the p21 H-ras 1 protein (LNPPDESGPGCMSCKCVLS (SEQ ID NO: 33); Capon et al., Nature 302:33 (1983)).

In a preferred embodiment, the targeting sequence is a lysozomal targeting sequence, including, for example, a lysosomal degradation sequence such as Lamp-2 (KFERQ (SEQ ID NO: 31); Dice, Ann. N.Y. Acad. Sci. 674:58 (1992); or lysosomal membrane sequences from Lamp-1 (MLIPIAGFFALAGLVLIVLIAYLIGRKRSHAGYOTI (SEQ ID NO: 32), Uthayakumar et al., Cell. Mol. Biol. Res. 41:405 (1995)) or Lamp-2 (LVPIAVGAALAGVLILVLLAYFIGLKHHHAGYEQF (SEQ ID NO: 33), Konecki et la., Biochem. Biophys. Res. Comm. 205:1–5 (1994), both of which show the transmembrane domains in italics and the cytoplasmic targeting signal underlined).

Alternatively, the targeting sequence may be a mitrochondrial localization sequence, including mitochondrial matrix sequences (e.g. yeast alcohol dehydrogenase III; MLRTSS-LFTRRVQPSLFSRNILRLQST (SEQ ID NO: 34); Schatz, Eur. J. Biochem. 165:1–6 (1987)); mitochondrial inner membrane sequences (yeast cytochrome c oxidase subunit IV; MLSLRQSIRFFKPATRTLCSSRYLL (SEQ ID NO: 35); Schatz, supra); mitochondrial intermembrane space sequences (yeast cytochrome c1; MFSMLSKRWAQRTL SKSFYSTATGAASKSGKLTQKLVTAGVAAAGITASTL LYADSLTAEAMTA (SEQ ID NO: 36); Schatz, supra) or mitochondrial outer membrane sequences (yeast 70 kD outer membrane protein; MKSFITRNKTAILATVAATG TAIGAYYYYNQLQQQQQRGKK (SEQ ID NO: 37); Schatz, supra).

The target sequences may also be endoplasmic reticulum sequences, including the sequences from calreticulin (KDEL (SEQ ID NO: 38); Pelham, Royal Society London Transactions B; 1–10 (1992)) or adenovirus E3/19K protein (LYLSRRSFIDEKKMP (SEQ ID NO: 39); Jackson et al., EMBO J. 9:3153 (1990). Furthermore, targeting sequences also include peroxisome sequences (for example, the peroxisome matrix sequence from Luciferase; SKL; Keller et al., PNAS U.S.A. 4:3264 (1987)); farnesylation sequences (for example, P21 H-ras 1; LNPPDESGPGCMSCKCVLS (SEQ ID NO: 40), with the bold cysteine farnesylated; Capon, supra); geranylgeranylation sequences (for example, protein rab-5A; LTEPTQPTRNQCCSN (SEQ ID NO: 41), with the bold cysteines geranylgeranylated; Farnsworth, PNAS U.S.A. 91:11963 (1994)); or destruction sequences (cyclin B1; RTALGDIGN (SEQ ID NO: 42); Klotzbucher et al., EMBO J. 1:3053 (1996)).

In a preferred embodiment, the targeting sequence is a secretory signal sequence capable of effecting the secretion of the peptide. There are a large number of known secretory signal sequences which are placed 5' to the variable peptide region, and are cleaved from the peptide region to effect secretion into the extracellular space. Secretory signal sequences and their transferability to unrelated proteins are well known, e.g., Silhavy, et al. (1985) Microbiol. Rev. 49, 398–418. This is particularly useful to generate a peptide capable of binding to the surface of, or affecting the physiology of, a target cell that is other than the host cell, e.g., the cell infected with the retrovirus. In a preferred approach, a fusion product is configured to contain, in series, secretion signal peptide-presentation structure-randomized expression product region-presentation structure, see FIG. 3. In this manner, target cells grown in the vicinity of cells caused to express the library of peptides, are bathed in secreted peptide. Target cells exhibiting a physiological change in response to the presence of a peptide, e.g., by the peptide binding to a surface receptor or by being internalized and binding to intracellular targets, and the secreting cells are localized by any of a variety of selection schemes and the peptide causing the effect determined. Exemplary effects include variously that of a designer cytokine (i.e., a stem cell factor capable of causing hematopoletic stem cells to divide and maintain their totipotential), a factor causing cancer cells to undergo spontaneous apoptosis, a factor that binds to the cell surface of target cells and labels them specifically, etc.

Suitable secretory sequences are known, including signals from IL-2 (MYRMQLLSCIALSLALVTNS (SEQ ID NO: 43); Villinger et al., J. Immunol. 155:3946 (1995)), growth hormone (MATGSRTSLLLAFGLLCLPWLQEGSAFPT (SEQ ID NO: 44); Roskam et al., Nucleic Acids Res. 7:30 (1979)); preproinsulin (MALWMRLLPLLALLALWGPDPAAAFVN (SEQ ID NO: 45); Bell et al., Nature 284:26 (1980)); and influenza HA protein (MKAKLLVLLYAFVAG<u>DQI</u> (SEQ ID NO: 46); Sekiwawa et al., PNAS 80:3563)), with cleavage between the non-underlined-underlined junction. A particularly preferred secretory signal sequence is the signal leader sequence from the secreted cytokine IL4, which comprises the first 24 amino acids of IL-4 as follows: MGLTSQLLPPLFFLLACAGNFVHG (SEQ ID NO: 47).

In a preferred embodiment, the fusion partner is a rescue sequence. A rescue sequence is a sequence which may be used to purify or isolate either the peptide or the nucleic acid encoding it. Thus, for example, peptide rescue sequences include purification sequences such as the $His_6$ tag for use with Ni affinity columns and epitope tags for detection, immunoprecipitation or FACS (fluoroscence-activated cell sorting). Suitable epitope tags include myc (for use with the commercially available 9E10 antibody), the BSP biotinylation target sequence of the bacterial enzyme BirA, flu tags, lacZ, GST, and Strep tag I and II.

Alternatively, the rescue sequence may be a unique oligonucleotide sequence which serves as a probe target site to allow the quick and easy isolation of the retroviral construct, via PCR, related techniques, or hybridization.

In a preferred embodiment, the fusion partner is a stability sequence to confer stability to the peptide or the nucleic acid encoding it. Thus, for example, peptides may be stabilized by the incorporation of glycines after the initiation methionine (MG or MGGO), for protection of the peptide to ubiquitination as per Varshavsky's N-End Rule, thus conferring long half-life in the cytoplasm. Similarly, two prolines at the C-terminus impart peptides that are largely resistant to carboxypeptidase action. The presence of two glycines prior to the prolines impart both flexibility and prevent structure initiating events in the di-proline to be propagated into the peptide structure. Thus, preferred stability sequences are as follows: $MG(X)_nGGPP$ (SEQ ID NO: 48), where X is any amino acid and n is an integer of at least four.

The fusion partners may be placed anywhere (i.e. N-terminal, C-terminal, internal) in the structure as the biology and activity permits. In addition, while the discussion has been directed to the fusion of fusion partners to the peptide portion of the fusion polypeptide, it is also possible to fuse one or more of these fusion partners to the GFP portion of the fusion polypeptide. Thus, for example, the GFP may contain a targeting sequence (either N-terminally, C-terminally, or internally, as described below) at one location, and a rescue sequence in the same place or a different place on the molecule. Thus, any combination of fusion partners and peptides and GFP proteins may be made.

In a preferred embodiment, the fusion partner includes a linker or tethering sequence. Linker sequences between various targeting sequences (for example, membrane targeting sequences) and the other components of the constructs (such as the randomized peptides) may be desirable to allow the peptides to interact with potential targets unhindered. For example, useful linkers include glycine polymers $(G)_n$, glycine-serine polymers (including, for example, $(GS)_n$, $(GSGGS)_n$ (SEQ ID NO: 49) and $(GGGS)_n$ (SEQ ID NO: 50), where n is an integer of at least one), glycine-alanine polymers, alanine-serine polymers, and other flexible linkers such as the tether for the shaker potassium channel, and a large variety of other flexible linkers, as will be appreciated by those in the art. Glycine and glycine-serine polymers are preferred since both of these amino acids are relatively unstructured, and therefore may be able to serve as a neutral tether between components. Glycine polymers are the most preferred as glycine accesses significantly more phi-psi space than even alanine, and is much less restricted tan residues with longer side chains (see Scheraga, Rev. Computational Chem. 11173–142 (1992)). Secondly, serine is hydrophilic and therefore able to solubilize what could be a globular glycine chain. Third, similar chains have been shown to be effective in joining subunits of recombinant proteins such as single chain antibodies.

In a preferred embodiment, the peptide is connected to the GFP via linkers. That is, while one embodiment utilizes the direct linkage of the peptide to the GFP, or of the peptide and any fusion partners to the GFP, a preferred embodiment utilizes linkers at one or both ends of the peptide. That is, when attached either to the N- or C-terminus, one linker may be used. When the peptide is inserted in an internal position, as is generally outlined below, preferred embodiments utilize at least one linker and preferably two, one at each terminus of the peptide. Linkers are generally preferred in order to conformationally decouple any insertion sequence (i.e. the peptide) from the GFP structure itself, to minimize local distortions in the GFP structure that can either destabilize folding intermediates or allow access to GFP's buried tripeptide fluorophore, which decreases (or eliminates) GFP's fluorescence due to exposure to exogeneous collisional fluorescence quenchers (see Phillips, Curr. Opin. Structural Biology 7:821 (1997), hereby incorporated by reference in its entireity).

Accordingly, as outlined below, when the peptides are inserted into internal positions in GFP, preferred embodiments utilize linkers, and preferably (gly)n linkers, where n is 1 or more, with n being two, three, four, five and six, although linkers of 7–10 or more amino acids are also possible. Generally in this embodiment, no amino acids with beta carbons are used in the linkers.

In addition, the fusion partners, including presentation structures, may be modified, randomized, and/or matured to alter the presentation orientation of the randomized expression product. For example, determinants at the base of the loop may be modified to slightly modify the internal loop peptide tertiary structure, which maintaining the randomized amino acid sequence.

In a preferred embodiment, combinations of fusion partners are used. Thus, for example, any number of combinations of presentation structures, targeting sequences, rescue sequences, and stability sequences may be used, with or without linker sequences. As will be appreciated by those in the art, using a base vector that contains a cloning site for receiving random and/or biased libraries, one can cassette in various fusion partners 5' and 3' of the library. In addition, as discussed herein, it is possible to have more than one variable region in a construct, either to together form a new surface or to bring two other molecules together. Similarly, as more fully outlined below, it is possible to have peptides inserted at two or more different loops of the GFP, preferably but not required to be on the same "face" of GFP.

In a preferred embodiment, the random peptide is fused to the N-terminus of the GFP. The fusion can be direct, i.e. with no additional residues between the C-terminus of the peptide and the N-terminus of the GFP, or indirect; that is, intervening amino acids are used, such as one or more fusion partners, including a linker. In this embodiment, preferably a presentation structure is used, to confer some conformational stability to the peptide. Particularly preferred embodiments include the use of dimerization sequences.

In one embodiment, N-terminal residues of the GFP are deleted, i.e. one or more amino acids of the GFP can be deleted and replaced with the peptide. However, as noted above, deletions of more than 7 amino acids may render the GFP less fluorescent, and thus larger deletions are generally not preferred. In a preferred embodiment, the fusion is directly to the first amino acid of the GFP.

In a preferred embodiment, the random peptide is fused to the C-terminus of the GFP. As above for N-terminal fusions, the fusion can be direct or indirect, and C-terminal residues may be deleted.

In a preferred embodiment, peptides and fusion partners are added to both the N- and the C-terminus of the GFP. As the N- and C-terminus of GFP are on the same "face" of the protein, in spatial proximity (within 18 Å), it is possible to make a non-covalently "circular" GFP protein using the components of the invention. Thus for example, the use of dimerization sequences can allow a noncovalently cyclized protein; by attaching a first dimerization sequence to either the N- or C-terminus of GFP, and adding a random peptide and a second dimerization sequence to the other terminus, a large compact structure can be formed.

In a preferred embodiment, the random peptide is fused to an internal position of the GFP; that is, the peptide is inserted at an internal position of the GFP. While the peptide can be inserted at virtually any position, preferred positions include insertion at the very tips of "loops" on the surface of the GFP, to minimize disruption of the GFP beta-can protein structure. In a preferred embodiment, loops are selected as having the highest temperature factors in the crystal structure as outlined in the Examples.

In a preferred embodiment, the random peptide is inserted, without any deletion of GFP residues. That is, the insertion point is between two amino acids in the loop, adding the new amino acids of the peptide and fusion partners, including linkers. Generally, when linkers are used, the linkers are directly fused to the GFP, with additional fusion partners, if present, being fused to the linkers and the peptides.

In a preferred embodiment, the peptide is inserted into the GFP, with one or more GFP residues being deleted; that is, the random peptide (and fusion partners, including linkers) replaces one or more residues. In general, when linkers are used, the linkers are attached directly to the GFP, thus it is linker residues which replace the GFP residues, again generally at the tip of the loop. In general, when residues are replaced, from one to five residues of GFP are deleted, with deletions of one, two, three, four and five amino acids all possible. Specific preferred deletions are outlined below.

Preferred insertion points in loops include, but are not limited to, loop 1 (amino acids 130–135), loop 2 (amino acids 154–159), loop 3 (amino acids 172–175), loop 4 (amino acids 188–193), and loop 5 (amino acids 208–216).

Particularly preferred embodiments include insertion of peptides and associated structures into loop 1, amino acids 130–135. In a preferred embodiment, one or more of the loop amino acids are deleted, with the deletion of asp133 being preferred.

In a preferred embodiment, peptides (and fusion partners, if present), are inserted into loop 2, amino acids 154–159. In a preferred embodiment, one or more of the loop amino acids are deleted, with the deletion of both lys156 and gln157 being preferred.

In a preferred embodiment, peptides (and fusion partners, if present), are inserted into loop 3, amino acids 172–175. In a preferred embodiment, one or more of the loop amino acids are deleted, with the deletion of asp173 being preferred.

In a preferred embodiment, peptides (and fusion partners, if present), are inserted into loop 4, amino acids 188–193. In a preferred embodiment, one or more of the loop amino acids are deleted, with the simultaneous deletion of gly189, asp190, gly191, and pro192 being preferred.

In a preferred embodiment, peptides (and fusion partners, if present), are inserted into loop 5, amino acids 208–216. In a preferred embodiment, one or more of the loop amino acids are deleted, with the simultaneous deletion of asn212, glu213 and lys214 being preferred.

In a preferred embodiment, peptides (including fusion partners, if applicable) can be inserted into more than one loop at a time. Thus, for example, adding peptides to both loops 2 and 4 can increase the complexity of the library but still allow presentation of these loops on the same face of the protein. Similarly, it is possible to add peptides to one or more loops and add other fusion partners to other loops, such as targeting sequences, etc.

Thus, fusion polypeptides comprising GFP and random peptides are provided. In addition, to facilitate the introduction of random peptides into the GFP, a preferred embodiment provides GFP proteins with a multisite cloning site inserted into at least one loop outlined above.

The invention further provides fusion nucleic acids encoding the fusion polypeptides of the invention. As will be appreciated by those in the art, due to the degeneracy of the genetic code, an extremely large number of nucleic acids may be made, all of which encode the fusion proteins of the present invention. Thus, having identified a particular amino acid sequence, those skilled in the art could make any number of different nucleic acids, by simply modifying the sequence of one or more codons in a way which does not change the amino acid sequence of the fusion protein.

Using the nucleic acids of the present invention which encode a fusion protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the fusion protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the fusion protein; for example, transcriptional and translational regulatory nucleic acid sequences from Bacillus are preferably used to express the fusion protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention. In a preferred embodiment, the promoters are strong promoters, allowing high expression in cells, particularly mammalian cells, such as the CMV promoter, particularly in combination with a Tet regulatory element.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

The candidate nucleic acids are introduced into the cells for screening, as is more fully outlined below. By "introduced into " or grammatical equivalents herein is meant that the nucleic acids enter the cells in a manner suitable for subsequent expression of the nucleic acid. The method of introduction is largely dictated by the targeted cell type, discussed below. Exemplary methods include $CaPO_4$ precipitation, liposome fusion, lipofectin®, electroporation, viral infection, etc. The candidate nucleic acids may stably integrate into the genome of the host cell (for example, with retroviral introduction, outlined below), or may exist either transiently or stably in the cytoplasm (i.e. through the use of traditional plasmids, utilizing standard regulatory sequences, selection markers, etc.). As many pharmaceutically important screens require human or model mammalian cell targets, retroviral vectors capable of transfecting such targets are preferred.

The fusion proteins of the present invention are produced by culturing a host cell transformed with an expression vector containing nucleic acid encoding a fusion protein, under the appropriate conditions to induce or cause expression of the fusion protein. The conditions appropriate for fusion protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli, Bacillus subtilis*, SF9 cells, C129 cells, 293 cells, Neurospora, BHK, CHO, COS, and HeLa cells, fibroblasts, Schwanoma cell lines, immortalized mammalian myeloid and lymphoid cell lines, Jurkat cells, mast cells and other endocrine and exocrine cells, and neuronal cells.

In a preferred embodiment, the fusion proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for the fusion protein into mRNA. A promoter will have a transcription initiating region, which is usually placed Oproximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei. As outlined herein, a particularly preferred method utilizes retroviral infection, as outlined in PCT US97/01019, incorporated by reference.

As will be appreciated by those in the art, the type of mammalian cells used in the present invention can vary widely. Basically, any mammalian cells may be used, with mouse, rat, primate and human cells being particularly preferred, although as will be appreciated by those in the art, modifications of the system by pseudotyping allows all eukaryotic cells to be used, preferably higher eukaryotes. As is more fully described below, a screen will be set up such that the cells exhibit a selectable phenotype in the presence of a bioactive peptide. As is more fully described below, cell types implicated in a wide variety of disease conditions are particularly useful, so long as a suitable screen may be designed to allow the selection of cells that exhibit an altered phenotype as a consequence of the presence of a peptide within the cell. Accordingly, suitable cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, etc. See the ATCC cell line catalog, hereby expressly incorporated by reference.

In one embodiment, the cells may be additionally genetically engineered, that is, contain exogeneous nucleic acid other than the fusion nucleic acid.

In a preferred embodiment, the fusion proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of the fusion protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the fusion protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcium chloride treatment, electroporation, and others.

In one embodiment, fusion proteins are produced in insect cells. Expression vectors for the transformation of insect cells, and in particular, baculovirus-based expression vectors, are well known in the art.

In a preferred embodiment, fusion protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K lactis, Pichia guillerimondii* and *P. pastoris, Schizosaccharomyces pombe,* and *Yarrowia lipolytica*. Preferred promoter sequences for expression in yeast include the inducible GAL1, 10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

In addition, the fusion polypeptides of the invention may be further fused to other proteins, if desired, for example to increase expression.

In one embodiment, the fusion nucleic acids, proteins and antibodies of the invention are labeled with a label other than the GFP. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

The fusion nucleic acids are introduced into the cells to screen for peptides capable of altering the phenotype of a cell.

In a preferred embodiment, a first plurality of cells is screened. That is, the cells into which the fusion nucleic acids are introduced are screened for an altered phenotype. Thus, in this embodiment, the effect of the bioactive peptide is seen in the same cells in which it is made; i.e. an autocrine effect.

By a "plurality of cells" herein is meant roughly from about $10^3$ cells to $10^8$ or $10^9$, with from $10^6$ to $10^8$ being preferred. This plurality of cells comprises a cellular library, wherein generally each cell within the library contains a member of the peptide molecular library, i.e. a different peptide (or nucleic acid encoding the peptide), although as will be appreciated by those in the art, some cells within the library may not contain a peptide, and some may contain more than species of peptide. When methods other than retroviral infection are used to introduce the candidate nucleic acids into a plurality of cells, the distribution of candidate nucleic acids within the individual cell members of the cellular library may vary widely, as it is generally difficult to control the number of nucleic acids which enter a cell during electroporation, etc.

In a preferred embodiment, the fusion nucleic acids are introduced into a first plurality of cells, and the effect of the peptide is screened in a second or third plurality of cells, different from the first plurality of cells, i.e. generally a different cell type. That is, the effect of the bioactive peptide is due to an extracellular effect on a second cell; i.e. an endocrine or paracrine effect. This is done using standard techniques. The first plurality of cells may be grown in or on one media, and the media is allowed to touch a second plurality of cells, and the effect measured. Alternatively, there may be direct contact between the cells. Thus, "contacting" is functional contact, and includes both direct and indirect. In this embodiment, the first plurality of cells may or may not be screened.

If necessary, the cells are treated to conditions suitable for the expression of the peptide (for example, when inducible promoters are used).

Thus, the methods of the present invention comprise introducing a molecular library of fusion nucleic acids encoding randomized peptides fused to GFP into a plurality of cells, a cellular library. Each of the nucleic acids comprises a different nucleotide sequence encoding GFP with a random peptide. The plurality of cells is then screened, as is more fully outlined below, for a cell exhibiting an altered phenotype. The altered phenotype is due to the presence of a bioactive peptide.

By "altered phenotype" or "changed physiology" or other grammatical equivalents herein is meant that the phenotype of the cell is altered in some way, preferably in some detectable and/or measurable way. As will be appreciated in the art, a strength of the present invention is the wide variety of cell types and potential phenotypic changes which may be tested using the present methods. Accordingly, any phenotypic change which may be observed, detected, or measured may be the basis of the screening methods herein. Suitable phenotypic changes include, but are not limited to: gross physical changes such as changes in cell morphology, cell growth, cell viability, adhesion to substrates or other cells, and cellular density; changes in the expression of one or more RNAs, proteins, lipids, hormones, cytokines, or other molecules; changes in the equilibrium state (i.e. half-life) or one or more RNAs, proteins, lipids, hormones, cytokines, or other molecules; changes in the localization of one or more RNAs, proteins, lipids, hormones, cytokines, or other molecules; changes in the bioactivity or specific activity of one or more RNAs, proteins, lipids, hormones, cytokines, receptors, or other molecules; changes in the secretion of ions, cytokines, hormones, growth factors, or other molecules; alterations in cellular membrane potentials, polarization, integrity or transport; changes in infectivity, susceptability, latency, adhesion, and uptake of viruses and bacterial pathogens; etc. By "capable of altering the phenotype" herein is meant that the bioactive peptide can change the phenotype of the cell in some detectable and/or measurable way.

The altered phenotype may be detected in a wide variety of ways, as is described more fully below, and will generally depend and correspond to the phenotype that is being changed. Generally, the changed phenotype is detected using, for example: microscopic analysis of cell morphology; standard cell viability assays, including both increased cell death and increased cell viability, for example, cells that are now resistant to cell death via virus, bacteria, or bacterial or synthetic toxins; standard labeling assays such as fluorometric indicator assays for the presence or level of a particular cell or molecule, including FACS or other dye staining techniques; biochemical detection of the expression of target compounds after killing the cells; etc. In some cases, as is more fully described herein, the altered phenotype is detected in the cell in which the fusion nucleic acid was introduced; in other embodiments, the altered phenotype is detected in a second cell which is responding to some molecular signal from the first cell.

An altered phenotype of a cell indicates the presence of a bioactive peptide, acting preferably in a transdominant way. By "transdominant" herein is meant that the bioactive peptide indirectly causes the altered phenotype by acting on a second molecule, which leads to an altered phenotype. That is, a transdominant expression product has an effect that is not in cis, i.e., a trans event as defined in genetic terms or biochemical terms. A transdominant effect is a distinguishable effect by a molecular entity (i.e., the encoded peptide or RNA) upon some separate and distinguishable target; that is, not an effect upon the encoded entity itself. As such, transdominant effects include many well-known effects by pharmacologic agents upon target molecules or pathways in cells or physiologic systems; for instance, the β-lactam antibiotics have a transdominant effect upon peptidoglycan synthesis in bacterial cells by binding to penicillin binding proteins and disrupting their functions. An exemplary transdominant effect by a peptide is the ability to inhibit NF-κB signaling by binding to IκB-α at a region critical for its function, such that in the presence of sufficient amounts of the peptide (or molecular entity), the signaling pathways that normally lead to the activation of NF-κB through phosphorylation and/or degradation of IκB-α are inhibited from acting at IκB-α because of the binding of the peptide or molecular entity. In another instance, signaling pathways that are normally activated to secrete IgE are inhibited in the presence of peptide. Or, signaling pathways in adipose tissue cells, normally quiescent, are activated to metabolize fat. Or, in the presence of a peptide, intracellular mechanisms for the replication of certain viruses, such as HIV-1, or Herpes viridae family members, or Respiratory Syncytia Virus, for example, are inhibited.

A transdominant effect upon a protein or molecular pathway is clearly distinguishable from randomization, change, or mutation of a sequence within a protein or molecule of known or unknown function to enhance or diminish a biochemical ability that protein or molecule already manifests. For instance, a protein that enzymatically cleaves β-lactam antibiotics, a β-lactamase, could be enhanced or diminished in its activity by mutating sequences internal to its structure that enhance or diminish the ability of this enzyme to act upon and cleave β-lactam antibiotics. This would be called a cis mutation to the protein. The effect of this protein upon β-lactam antibiotics is an activity the protein already manifests, to a distinguishable degree. Similarly, a mutation in the leader sequence that enhanced the export of this protein to the extracellular spaces wherein it might encounter β-lactam molecules more readily, or a mutation within the sequence that enhance the stability of the protein, would be termed cis mutations in the protein. For comparison, a transdominant effector of this protein would include an agent, independent of the β-lactamase, that bound to the β-lactamase in such a way that it enhanced or diminished the function of the β-lactamase by virtue of its binding to β-lactamase.

In a preferred embodiment, once a cell with an altered phenotype is detected, the presence of the fusion protein is verified, to ensure that the peptide was expressed and thus that the altered phenotype can be due to the presence of the peptide. As will be appreciated by those in the art, this verification of the presence of the peptide can be done either before, during or after the screening for an altered phenotype. This can be done in a variety of ways, although preferred methods utilize FACS techniques. Once the presence of the fusion protein is verified, the cell with the altered phenotype is generally isolated from the plurality which do not have altered phenotypes. This may be done in any number of ways, as is known in the art, and will in some instances depend on the assay or screen. Suitable isolation techniques include, but are not limited to, FACS, lysis selection using complement, cell cloning, scanning by Fluorimager, expression of a "survival" protein, induced expression of a cell surface protein or other molecule that can be rendered fluorescent or taggable for physical isolation; expression of an enzyme that changes a non-fluorescent molecule to a fluorescent one; overgrowth against a background of no or slow growth; death of cells and isolation of DNA or other cell vitality indicator dyes, etc.

In a preferred embodiment, the fusion nucleic acid and/or the bioactive peptide (i.e. the fusion protein) is isolated from the positive cell. This may be done in a number of ways. In a preferred embodiment, primers complementary to DNA regions common to the retroviral constructs, or to specific components of the library such as a rescue sequence, defined above, are used to "rescue" the unique random sequence. Alternatively, the fusion protein is isolated using a rescue sequence. Thus, for example, rescue sequences comprising epitope tags or purification sequences may be used to pull out the fusion protein using immunoprecipitation or affinity columns. In some instances, as is outlined below, this may also pull out the primary target molecule, if there is a sufficiently strong binding interaction between the bioactive peptide and the target molecule. Alternatively, the peptide may be detected using mass spectroscopy.

Once rescued, the sequence of the bioactive peptide and/or fusion nucleic acid is determined. This information can then be used in a number of ways.

In a preferred embodiment, the bioactive peptide is resynthesized and reintroduced into the target cells, to verify the effect. This may be done using retroviruses, or alternatively using fusions to the HIV-1 Tat protein, and analogs and related proteins, which allows very high uptake into target cells. See for example, Fawell et al., PNAS U.S.A. 91:664 (1994); Frankel et al., Cell 55:1189 (1988); Savion et al., J. Biol. Chem. 256:1149(1981); Derossi et al., J. Biol. Chem. 269:10444 (1994); and Baldin et al., EMBO J. 9:1511 (1990), all of which are incorporated by reference.

In a preferred embodiment, the sequence of a bioactive peptide is used to generate more candidate peptides. For example, the sequence of the bioactive peptide may be the basis of a second round of (biased) randomization, to develop bioactive peptides with increased or altered activities. Alternatively, the second round of randomization may change the affinity of the bioactive peptide. Furthermore, it may be desirable to put the identified random region of the bioactive peptide into other presentation structures, or to alter the sequence of the constant region of the presentation structure, to alter the conformation/shape of the bioactive peptide. It may also be desirable to "walk" around a potential binding site, in a manner similar to the mutagenesis of a binding pocket, by keeping one end of the ligand region constant and randomizing the other end to shift the binding of the peptide around.

In a preferred embodiment, either the bioactive peptide or the bioactive nucleic acid encoding it is used to identify target molecules, i.e. the molecules with which the bioactive peptide interacts. As will be appreciated by those in the art, there may be primary target molecules, to which the bioactive peptide binds or acts upon directly, and there may be secondary target molecules, which are part of the signalling pathway affected by the bioactive peptide; these might be termed "validated targets".

In a preferred embodiment, the bioactive peptide is used to pull out target molecules. For example, as outlined herein, if the target molecules are proteins, the use of epitope tags or purification sequences can allow the purification of primary target molecules via biochemical means (co-immunoprecipitation, affinity columns, etc.). Alternatively, the peptide, when expressed in bacteria and purified, can be used as a probe against a bacterial cDNA expression library made from mRNA of the target cell type. Or, peptides can be used as "bait" in either yeast or mammalian two or three hybrid systems. Such interaction cloning approaches have been very useful to isolate DNA-binding proteins and other interacting protein components. The peptide(s) can be combined with other pharmacologic activators to study the epistatic relationships of signal transduction pathways in question. It is also possible to synthetically prepare labeled peptide and use it to screen a cDNA library expressed in bacteriophage for those cDNAs which bind the peptide. Furthermore, it is also possible that one could use cDNA cloning via retroviral libraries to "complement" the effect induced by the peptide. In such a strategy, the peptide would be required to be stochiometrically titrating away some important factor for a specific signaling pathway. If this molecule or activity is replenished by over-expression of a cDNA from within a cDNA library, then one can clone the target. Similarly, cDNAs cloned by any of the above yeast or bacteriophage systems can be reintroduced to mammalian cells in this manner to confirm that they act to complement function in the system the peptide acts upon.

Once primary target molecules have been identified, secondary target molecules may be identified in the same manner, using the primary target as the "bait". In this manner, signalling pathways may be elucidated. Similarly, bioactive peptides specific for secondary target molecules may also be discovered, to allow a number of bioactive peptides to act on a single pathway, for example for combination therapies.

The screening methods of the present invention may be useful to screen a large number of cell types under a wide variety of conditions. Generally, the host cells are cells that are involved in disease states, and they are tested or screened under conditions that normally result in undesirable consequences on the cells. When a suitable bioactive peptide is found, the undesirable effect may be reduced or eliminated. Alternatively, normally desirable consequences may be reduced or eliminated, with an eye towards elucidating the cellular mechanisms associated with the disease state or signalling pathway.

In a preferred embodiment, the present methods are useful in cancer applications. The ability to rapidly and specifically kill tumor cells is a cornerstone of cancer chemotherapy. In general, using the methods of the present invention, random libraries can be introduced into any tumor cell (primary or cultured), and peptides identified which by themselves induce apoptosis, cell death, loss of cell division or decreased cell growth. This may be done de novo, or by biased randomization toward known peptide agents, such as angiostatin, which inhibits blood vessel wall growth. Alternatively, the methods of the present invention can be combined with other cancer therapeutics (e.g. drugs or radiation) to sensitize the cells and thus induce rapid and specific apoptosis, cell death, loss of cell division or decreased cell growth after exposure to a secondary agent. Similarly, the present methods may be used in conjunction with known cancer therapeutics to screen for agonists to make the therapeutic more effective or less toxic. This is particularly preferred when the chemotherapeutic is very expensive to produce such as taxol.

Known oncogenes such as v-Abl, v-Src, v-Ras, and others, induce a transformed phenotype leading to abnormal cell growth when transfected into certain cells. This is also a major problem with micro-metastases. Thus, in a preferred embodiment, non-transformed cells can be transfected with these oncogenes, and then random libraries introduced into these cells, to select for bioactive peptides which reverse or correct the transformed state. One of the signal features of oncogene transformation of cells is the loss of contact inhibition and the ability to grow in soft-agar. When transforming viruses are constructed containing v-Abl, v-Src, or v-Ras in IRES-puro retroviral vectors, infected into target 3T3 cells, and subjected to puromycin selection, all of the 3T3 cells hyper-transform and detach from the plate. The cells may be removed by washing with fresh medium. This can serve as the basis of a screen, since cells which express a bioactive peptide will remain attached to the plate and form colonies.

Similarly, the growth and/or spread of certain tumor types is enhanced by stimulatory responses from growth factors and cytokines (PDGF, EGF, Heregulin, and others) which bind to receptors on the surfaces of specific tumors. In a preferred embodiment, the methods of the invention are used to inhibit or stop tumor growth and/or spread, by finding bioactive peptides capable of blocking the ability of the growth factor or cytokine to stimulate the tumor cell. The introduction of random libraries into specific tumor cells with the addition of the growth factor or cytokine, followed by selection of bioactive peptides which block the binding, signaling, phenotypic and/or functional responses of these tumor cells to the growth factor or cytokine in question.

Similarly, the spread of cancer cells (invasion and metastasis) is a significant problem limiting the success of cancer therapies. The ability to inhibit the invasion and/or migration of specific tumor cells would be a significant advance in the therapy of cancer. Tumor cells known to have a high metastatic potential (for example, melanoma, lung cell carcinoma, breast and ovarian carcinoma) can have random libraries introduced into them, and peptides selected which in a migration or invasion assay, inhibit the migration and/or invasion of specific tumor cells. Particular applications for inhibition of the metastatic phenotype, which could allow a more specific inhibition of metastasis, include the metastasis suppressor gene NM23, which codes for a dinucleoside diphosphate kinase. Thus intracellular peptide activators of this gene could block metastasis, and a screen for its upregulation (by fusing it to a reporter gene) would be of interest. Many oncogenes also enhance metastasis. Peptides which inactivate or counteract mutated RAS oncogenes, v-MOS, v-RAF, A-RAF, v-SRC, v-FES, and v-FMS would also act as anti-metastatics. Peptides which act intracellularly to block the release of combinations of proteases required for invasion, such as the matrix metalloproteases and urokinase, could also be effective antimetastatics.

In a preferred embodiment, the random libraries of the present invention are introduced into tumor cells known to have inactivated tumor suppressor genes, and successful reversal by either reactivation or compensation of the knockout would be screened by restoration of the normal phenotype. A major example is the reversal of p53-inactivating mutations, which are present in 50% or more of all cancers. Since p53's actions are complex and involve its action as a transcription factor, there are probably numerous potential ways a peptide or small molecule derived from a peptide could reverse the mutation. One example would be upregulation of the immediately downstream cyclin-dependent kinase p21CIP1/WAF1. To be useful such reversal would have to work for many of the different known p53 mutations. This is currently being approached by gene therapy; one or more small molecules which do this might be preferable.

Another example involves screening of bioactive peptides which restore the constitutive function of the brca-1 or brca-2 genes, and other tumor suppressor genes important in breast cancer such as the adenomatous polyposis coli gene (APC) and the Drosophila discs-large gene (Dlg), which are components of cell-cell junctions. Mutations of brca-1 are important in hereditary ovarian and breast cancers, and constitute an additional application of the present invention.

In a preferred embodiment, the methods of the present invention are used to create novel cell lines from cancers from patients. A retrovirally delivered short peptide which inhibits the final common pathway of programmed cell death should allow for short- and possibly long-term cell lines to be established. Conditions of in vitro culture and infection of human leukemia cells will be established. There is a real need for methods which allow the maintenance of certain tumor cells in culture long enough to allow for physiological and pharmacological studies. Currently, some human cell lines have been established by the use of transforming agents such as Ebstein-Barr virus that considerably alters the existing physiology of the cell. On occasion, cells will grow on their own in culture but this is a random event. Programmed cell death (apoptosis) occurs via complex signaling pathways within cells that ultimately activate a final common pathway producing characteristic changes in the cell leading to a non-inflammatory destruction of the cell. It is well known that tumor cells have a high apoptotic index, or propensity to enter apoptosis in vivo. When cells are placed in culture, the in vivo stimuli for malignant cell growth are removed and cells readily undergo apoptosis. The objective would be to develop the technology to establish cell lines from any number of primary tumor cells, for example primary human leukemia cells, in a reproducible manner without altering the native configuration of the signaling pathways in these cells. By introducing nucleic acids encoding peptides which inhibit apoptosis, increased cell survival in vitro, and hence the opportunity to study signalling transduction pathways in primary human tumor cells, is accomplished. In addition, these methods may be used for culturing primary cells, i.e. non-tumor cells.

In a preferred embodiment, the present methods are useful in cardiovascular applications. In a preferred embodiment, cardiomyocytes may be screened for the prevention of cell damage or death in the presence of normally injurious conditions, including, but not limited to, the presence of toxic drugs (particularly chemotherapeutic drugs), for example, to prevent heart failure following treatment with adriamycin; anoxia, for example in the setting of coronary artery occlusion; and autoimmune cellular damage by attack from activated lymphoid cells (for example as seen in post viral myocarditis and lupus). Candidate bioactive peptides are inserted into cardiomyocytes, the cells are subjected to the insult, and bioactive peptides are selected that prevent any or all of: apoptosis; membrane depolarization (i.e. decrease arrythmogenic potential of insult); cell swelling; or leakage of specific intracellular ions, second messengers and activating molecules (for example, arachidonic acid and/or lysophosphatidic acid).

In a preferred embodiment, the present methods are used to screen for diminished arrhythmia potential in cardiomyocytes. The screens comprise the introduction of the candidate nucleic acids encoding candidate bioactive peptides, followed by the application of arrythmogenic insults, with screening for bioactive peptides that block specific depolarization of cell membrane. This may be detected using patch clamps, or via fluorescence techniques). Similarly, channel activity (for example, potassium and chloride channels) in cardiomyocytes could be regulated using the present methods in order to enhance contractility and prevent or diminish arrhythmias.

In a preferred embodiment, the present methods are used to screen for enhanced contractile properties of cardiomyocytes and diminish heart failure potential. The introduction of the libraries of the invention followed by measuring the rate of change of myosin polymerization/depolymerization using fluorescent techniques can be done. Bioactive peptides which increase the rate of change of this phenomenon can result in a greater contractile response of the entire myocardium, similar to the effect seen with digitalis.

In a preferred embodiment, the present methods are useful to identify agents that will regulate the intracellular and sarcolemmal calcium cycling in cardiomyocytes in order to prevent arrhythmias. Bioactive peptides are selected that regulate sodium-calcium exchange, sodium proton pump function, and regulation of calcium-ATPase activity.

In a preferred embodiment, the present methods are useful to identify agents that diminish embolic phenomena in arteries and arterioles leading to strokes (and other occlusive events leading to kidney failure and limb ischemia) and angina precipitating a myocardial infarct are selected. For example, bioactive peptides which will diminish the adhesion of platelets and leukocytes, and thus diminish the occlusion events. Adhesion in this setting can be inhibited by the libraries of the invention being inserted into endothelial cells (quiescent cells, or activated by cytokines, i.e. IL-1, and growth factors, i.e. PDGF/EGF) and then screening for peptides that either: 1) downregulate adhesion molecule expression on the surface of the endothelial cells (binding assay); 2) block adhesion molecule activation on the surface of these cells (signaling assay); or 3) release in an autocrine manner peptides that block receptor binding to the cognate receptor on the adhering cell.

Embolic phenomena can also be addressed by activating proteolytic enzymes on the cell surfaces of endothelial cells, and thus releasing active enzyme which can digest blood clots. Thus, delivery of the libraries of the invention to endothelial cells is done, followed by standard fluorogenic assays, which will allow monitoring of proteolytic activity on the cell surface towards a known substrate. Bioactive peptides can then be selected which activate specific enzymes towards specific substrates.

In a preferred embodiment, arterial inflammation in the setting of vasculitis and post-infarction can be regulated by decreasing the chemotactic responses of leukocytes and mononuclear leukocytes. This can be accomplished by blocking chemotactic receptors and their responding pathways on these cells. Candidate bioactive libraries can be inserted into these cells, and the chemotactic response to diverse chemokines (for example, to the IL-8 family of chemokines, RANTES) inhibited in cell migration assays.

In a preferred embodiment, arterial restenosis following coronary angioplasty can be controlled by regulating the proliferation of vascular intimal cells and capillary and/or arterial endothelial cells. Candidate bioactive peptide libraries can be inserted into these cell types and their proliferation in response to specific stimuli monitored. One application may be intracellular peptides which block the expression or function of c-myc and other oncogenes in smooth muscle cells to stop their proliferation. A second application may involve the expression of libraries in vascular smooth muscle cells to selectively induce their apoptosis. Application of small molecules derived from these peptides may require targeted drug delivery; this is available with stents, hydrogel coatings, and infusion-based catheter systems. Peptides which downregulate endothelin-1A receptors or which block the release of the potent vasoconstrictor and vascular smooth muscle cell mitogen endothelin-1 may also be candidates for therapeutics. Peptides can be isolated from these libraries which inhibit growth of these cells, or which prevent the adhesion of other cells in the circulation known to release autocrine growth factors, such as platelets (PDGF) and mononuclear leukocytes.

The control of capillary and blood vessel growth is an important goal in order to promote increased blood flow to ischemic areas (growth), or to cut-off the blood supply (angiogenesis inhibition) of tumors. Candidate bioactive peptide libraries can be inserted into capillary endothelial cells and their growth monitored. Stimuli such as low oxygen tension and varying degrees of angiogenic factors can regulate the responses, and peptides isolated that produce the appropriate phenotype. Screening for antagonism of vascular endothelial cell growth factor, important in angiogenesis, would also be useful.

In a preferred embodiment, the present methods are useful in screening for decreases in atherosclerosis producing mechanisms to find peptides that regulate LDL and HDL metabolism. Candidate libraries can be inserted into the appropriate cells (including hepatocytes, mononuclear leukocytes, endothelial cells) and peptides selected which lead to a decreased release of LDL or diminished synthesis of LDL, or conversely to an increased release of HDL or enhanced synthesis of HDL. Bioactive peptides can also be isolated from candidate libraries which decrease the production of oxidized LDL, which has been implicated in atherosclerosis and isolated from atherosclerotic lesions. This could occur by decreasing its expression, activating reducing systems or enzymes, or blocking the activity or production of enzymes implicated in production of oxidized LDL, such as 15-lipoxygenase in macrophages.

In a preferred embodiment, the present methods are used in screens to regulate obesity via the control of food intake mechanisms or diminishing the responses of receptor signaling pathways that regulate metabolism. Bioactive peptides that regulate or inhibit the responses of neuropeptide Y (NPY), cholecystokinin and galanin receptors, are particularly desirable. Candidate libraries can be inserted into cells that have these receptors cloned into them, and inhibitory peptides selected that are secreted in an autocrine manner that block the signaling responses to galanin and NPY. In a similar manner, peptides can be found that regulate the leptin receptor.

In a preferred embodiment, the present methods are useful in neurobiology applications. Candidate libraries may be used for screening for anti-apoptotics for preservation of neuronal function and prevention of neuronal death. Initial screens would be done in cell culture. One application would include prevention of neuronal death, by apoptosis, in cerebral ischemia resulting from stroke. Apoptosis is known to be blocked by neuronal apoptosis inhibitory protein (NAIP); screens for its upregulation, or effecting any coupled step could yield peptides which selectively block neuronal apoptosis. Other applications include neurodegenerative diseases such as Alzheimer's disease and Huntington's disease.

In a preferred embodiment, the present methods are useful in bone biology applications. Osteoclasts are known to play a key role in bone remodeling by breaking down "old" bone, so that osteoblasts can lay down "new" bone. In osteoporosis one has an imbalance of this process. Osteoclast overactivity can be regulated by inserting candidate libraries into these cells, and then looking for bioactive peptides that produce: 1) a diminished processing of collagen by these cells; 2) decreased pit formation on bone chips; and 3) decreased release of calcium from bone fragments.

The present methods may also be used to screen for agonists of bone morphogenic proteins, hormone mimetics to stimulate, regulate, or enhance new bone formation (in a manner similar to parathyroid hormone and calcitonin, for example). These have use in osteoporosis, for poorly healing fractures, and to accelerate the rate of healing of new fractures. Furthermore, cell lines of connective tissue origin can be treated with candidate libraries and screened for their growth, proliferation, collagen stimulating activity, and/or proline incorporating ability on the target osteoblasts. Alternatively, candidate libraries can be expressed directly in osteoblasts or chondrocytes and screened for increased production of collagen or bone.

In a preferred embodiment, the present methods are useful in skin biology applications. Keratinocyte responses to a variety of stimuli may result in psoriasis, a proliferative change in these cells. Candidate libraries can be inserted into cells removed from active psoriatic plaques, and bioactive peptides isolated which decrease the rate of growth of these cells.

In a preferred embodiment, the present methods are useful in the regulation or inhibition of keloid formation (i.e. excessive scarring). Candidate libraries inserted into skin connective tissue cells isolated from individuals with this condition, and bioactive peptides isolated that decrease proliferation, collagen formation, or proline incorporation. Results from this work can be extended to treat the excessive scarring that also occurs in bum patients. If a common peptide motif is found in the context of the keloid work, then it can be used widely in a topical manner to diminish scarring post bum.

Similarly, wound healing for diabetic ulcers and other chronic "failure to heal" conditions in the skin and extremities can be regulated by providing additional growth signals to cells which populate the skin and dermal layers. Growth factor mimetics may in fact be very useful for this condition. Candidate libraries can be inserted into skin connective tissue cells, and bioactive peptides isolated which promote the growth of these cells under "harsh" conditions, such as low oxygen tension, low pH, and the presence of inflammatory mediators.

Cosmeceutical applications of the present invention include the control of melanin production in skin melanocytes. A naturally occurring peptide, arbutin, is a tyrosine hydroxylase inhibitor, a key enzyme in the synthesis of melanin. Candidate libraries can be inserted into melanocytes and known stimuli that increase the synthesis of melanin applied to the cells. Bioactive peptides can be isolated that inhibit the synthesis of melanin under these conditions.

In a preferred embodiment, the present methods are useful in endocrinology applications. The retroviral peptide library technology can be applied broadly to any endocrine, growth factor, cytokine or chemokine network which involves a signaling peptide or protein that acts in either an endocrine, paracrine or autocrine manner that binds or dimerizes a receptor and activates a signaling cascade that results in a known phenotypic or functional outcome. The methods are applied so as to isolate a peptide which either mimics the desired hormone (i.e., insulin, leptin, calcitonin, PDGF, EGF, EPO, GMCSF, IL1-17, mimetics) or inhibits its action by either blocking the release of the hormone, blocking its binding to a specific receptor or carrier protein (for example, CRF binding protein), or inhibiting the intracellular responses of the specific target cells to that hormone. Selection of peptides which increase the expression or release of hormones from the cells which normally produce them could have broad applications to conditions of hormonal deficiency.

In a preferred embodiment, the present methods are useful in infectious disease applications. Viral latency (herpes viruses such as CMV, EBV, HBV, and other viruses such as HIV) and their reactivation are a significant problem, particularly in immunosuppressed patients ( patients with AIDS and transplant patients). The ability to block the reactivation and spread of these viruses is an important goal. Cell lines known to harbor or be susceptible to latent viral infection can be infected with the specific virus, and then stimuli applied to these cells which have been shown to lead to reactivation and viral replication. This can be followed by measuring viral titers in the medium and scoring cells for phenotypic changes. Candidate libraries can then be inserted into these cells under the above conditions, and peptides isolated which block or diminish the growth and/or release of the virus. As with chemotherapeutics, these experiments can also be done with drugs which are only partially effective towards this outcome, and bioactive peptides isolated which enhance the virucidal effect of these drugs.

One example of many is the ability to block HIV-1 infection. HIV-1 requires CD4 and a co-receptor which can be one of several seven transmembrane G-protein coupled receptors. In the case of the infection of macrophages, CCR-5 is the required co-receptor, and there is strong evidence that a block on CCR-5 will result in resistance to HIV-1 infection. There are two lines of evidence for this statement. First, it is known that the natural ligands for CCR-5, the CC chemokines RANTES, MIP1a and MIP1b are responsible for CD8+ mediated resistance to HIV. Second, individuals homozygous for a mutant allele of CCR-5 are completely resistant to HIV infection. Thus, an inhibitor of the CCR-5/HIV interaction would be of enormous interest to both biologists and clinicians. The extracellular anchored constructs offer superb tools for such a discovery. Into the transmembrane, epitope tagged, glycineserine tethered constructs (ssTM V G20 E TM), one can place a random, cyclized peptide library of the general sequence CNNNNNNNNNNC (SEQ ID NO: 51) or $C-(X)_n-C$. Then one infects a cell line that expresses CCR-5 with retroviruses containing this library. Using an antibody to CCR-5 one can use FACS to sort desired cells based on the binding of this antibody to the receptor. All cells which do not bind the antibody will be assumed contain inhibitors of this antibody binding site. These inhibitors, in the retroviral construct can be further assayed for their ability to inhibit HIV-1 entry.

Viruses are known to enter cells using specific receptors to bind to cells (for example, HIV uses CD4, coronavirus uses CD13, murine leukemia virus uses transport protein, and measles virus uses CD44) and to fuse with cells (HIV uses chemokine receptor). Candidate libraries can be inserted into target cells known to be permissive to these viruses, and bioactive peptides isolated which block the ability of these viruses to bind and fuse with specific target cells.

In a preferred embodiment, the present invention finds use with infectious organisms. Intracellular organisms such as mycobacteria, listeria, salmonella, pneumocystis, yersinia, leishmania, *T. cruzi*, can persist and replicate within cells, and become active in immunosuppressed patients. There are currently drugs on the market and in development which are either only partially effective or ineffective against these organisms. Candidate libraries can be inserted into specific cells infected with these organisms (pre- or post-infection), and bioactive peptides selected which promote the intracellular destruction of these organisms in a manner analogous to intracellular "antibiotic peptides" similar to magainins. In addition peptides can be selected which enhance the cidal properties of drugs already under investigation which have insufficient potency by themselves, but when combined with a specific peptide from a candidate library, are dramatically more potent through a synergistic mechanism. Finally, bioactive peptides can be isolated which alter the metabolism of these intracellular organisms, in such a way as to terminate their intracellular life cycle by inhibiting a key organismal event.

Antibiotic drugs that are widely used have certain dose dependent, tissue specific toxicities. For example renal toxicity is seen with the use of gentamicin, tobramycin, and amphotericin; hepatotoxicity is seen with the use of INH and rifampin; bone marrow toxicity is seen with chloramphenicol; and platelet toxicity is seen with ticarcillin, etc. These toxicities limit their use. Candidate libraries can be introduced into the specific cell types where specific changes leading to cellular damage or apoptosis by the antibiotics are produced, and bioactive peptides can be isolated that confer protection, when these cells are treated with these specific antibiotics.

Furthermore, the present invention finds use in screening for bioactive peptides that block antibiotic transport mechanisms. The rapid secretion from the blood stream of certain antibiotics limits their usefulness. For example penicillins are rapidly secreted by certain transport mechanisms in the kidney and choroid plexus in the brain. Probenecid is known to block this transport and increase serum and tissue levels. Candidate agents can be inserted into specific cells derived from kidney cells and cells of the choroid plexus known to have active transport mechanisms for antibiotics. Bioactive peptides can then be isolated which block the active transport of specific antibiotics and thus extend the serum halflife of these drugs.

In a preferred embodiment, the present methods are useful in drug toxicities and drug resistance applications. Drug toxicity is a significant clinical problem. This may manifest itself as specific tissue or cell damage with the result that the drug's effectiveness is limited. Examples include myeloablation in high dose cancer chemotherapy, damage to epithelial cells lining the airway and gut, and hair loss. Specific examples include adriamycin induced cardiomyocyte death, cisplatinin-induced kidney toxicity, vincristine-induced gut motility disorders, and cyclosporin-induced kidney damage. Candidate libraries can be introduced into specific cell types with characteristic drug-induced phenotypic or functional responses, in the presence of the drugs, and agents isolated which reverse or protect the specific cell type against the toxic changes when exposed to the drug. These effects may manifest as blocking the drug induced apoptosis of the cell of interest, thus initial screens will be for survival of the cells in the presence of high levels of drugs or combinations of drugs used in combination chemotherapy.

Drug toxicity may be due to a specific metabolite produced in the liver or kidney which is highly toxic to specific cells, or due to drug interactions in the liver which block or enhance the metabolism of an administered drug. Candidate libraries can be introduced into liver or kidney cells following the exposure of these cells to the drug known to produce the toxic metabolite. Bioactive peptides can be isolated which alter how the liver or kidney cells metabolize the drug, and specific agents identified which prevent the generation of a specific toxic metabolite. The generation of the metabolite can be followed by mass spectrometry, and phenotypic changes can be assessed by microscopy. Such a screen can also be done in cultured hepatocytes, cocultured with readout cells which are specifically sensitive to the toxic metabolite. Applications include reversible (to limit toxicity) inhibitors of enzymes involved in drug metabolism.

Multiple drug resistance, and hence tumor cell selection, outgrowth, and relapse, leads to morbidity and mortality in cancer patients. Candidate libraries can be introduced into tumor cell lines (primary and cultured) that have demonstrated specific or multiple drug resistance. Bioactive peptides can then be identified which confer drug sensitivity when the cells are exposed to the drug of interest, or to drugs used in combination chemotherapy. The readout can be the onset of apoptosis in these cells, membrane permeability changes, the release of intracellular ions and fluorescent markers. The cells in which multidrug resistance involves membrane transporters can be preloaded with fluorescent transporter substrates, and selection carried out for peptides which block the normal efflux of fluorescent drug from these cells. Candidate libraries are particularly suited to screening for peptides which reverse poorly characterized or recently discovered intracellular mechanisms of resistance or mechanisms for which few or no chemosensitizers currently exist, such as mechanisms involving LRP (lung resistance protein). This protein has been implicated in multidrug resistance in ovarian carcinoma, metastatic malignant melanoma, and acute myeloid leukemia. Particularly interesting examples include screening for agents which reverse more than one important resistance mechanism in a single cell, which occurs in a subset of the most drug resistant cells, which are also important targets. Applications would include screening for peptide inhibitors of both MRP (multidrug resistance related protein) and LRP for treatment of resistant cells in metastatic melanoma, for inhibitors of both p-glycoprotein and LRP in acute myeloid leukemia, and for inhibition (by any mechanism) of all three proteins for treating pan-resistant cells.

In a preferred embodiment, the present methods are useful in improving the performance of existing or developmental drugs. First pass metabolism of orally administered drugs limits their oral bioavailability, and can result in diminished efficacy as well as the need to administer more drug for a desired effect. Reversible inhibitors of enzymes involved in first pass metabolism may thus be a useful adjunct enhancing the efficacy of these drugs. First pass metabolism occurs in the liver, thus inhibitors of the corresponding catabolic enzymes may enhance the effect of the cognate drugs. Reversible inhibitors would be delivered at the same time as, or slightly before, the drug of interest. Screening of candidate libraries in hepatocytes for inhibitors (by any mechanism, such as protein downregulation as well as a direct inhibition of activity) of particularly problematical isozymes would be of interest. These include the CYP3A4 isozymes of cytochrome P450, which are involved in the first pass metabolism of the anti-HIV drugs saquinavir and indinavir. Other applications could include reversible inhibitors of UDP-glucuronyltransferases, sulfotransferases, N-acetyltransferases, epoxide hydrolases, and glutathione S-transferases, depending on the drug. Screens would be done in cultured hepatocytes or liver microsomes, and could involve antibodies recognizing the specific modification performed in the liver, or cocultured readout cells, if the metabolite had a different bioactivity than the untransformed drug. The enzymes modifying the drug would not necessarily have to be known, if screening was for lack of alteration of the drug.

In a preferred embodiment, the present methods are useful in immunobiology, inflammation, and allergic response applications. Selective regulation of T lymphocyte responses is a desired goal in order to modulate immune-mediated diseases in a specific manner. Candidate libraries can be introduced into specific T cell subsets (TH1, TH2, CD4+, CD8+, and others) and the responses which characterize those subsets (cytokine generation, cytotoxicity, proliferation in response to antigen being presented by a mononuclear leukocyte, and others) modified by members of the library. Agents can be selected which increase or diminish the known T cell subset physiologic response. This approach will be useful in any number of conditions, including: 1) autoimmune diseases where one wants to induce a tolerant state (select a peptide that inhibits T cell subset from recognizing a self-antigen bearing cell); 2) allergic diseases where one wants to decrease the stimulation of IgE producing cells (select peptide which blocks release from T cell subsets of specific B-cell stimulating cytokines which induce switch to IgE production); 3) in transplant patients where one wants to induce selective immunosuppression (select peptide that diminishes proliferative responses of host T cells to foreign antigens); 4) in lymphoproliferative states where one wants to inhibit the growth or sensitize a specific T cell tumor to chemotherapy and/or radiation; 5) in tumor surveillance where one wants to inhibit the killing of cytotoxic T cells by Fas ligand bearing tumor cells; and 5) in T cell mediated inflammatory diseases such as Rheumatoid arthritis, Connective tissue diseases (SLE), Multiple sclerosis, and inflammatory bowel disease, where one wants to inhibit the proliferation of disease-causing T cells (promote their selective apoptosis) and the resulting selective destruction of target tissues (cartilage, connective tissue, oligodendrocytes, gut endothelial cells, respectively).

Regulation of B cell responses will permit a more selective modulation of the type and amount of immunoglobulin made and secreted by specific B cell subsets. Candidate libraries can be inserted into B cells and bioactive peptides selected which inhibit the release and synthesis of a specific immunoglobulin. This may be useful in autoimmune diseases characterized by the overproduction of auto antibodies and the production of allergy causing antibodies, such as IgE. Agents can also be identified which inhibit or enhance the binding of a specific immunoglobulin subclass to a specific antigen either foreign of self. Finally, agents can be selected which inhibit the binding of a specific immunoglobulin subclass to its receptor on specific cell types.

Similarly, agents which affect cytokine production may be selected, generally using two cell systems. For example, cytokine production from macrophages, monocytes, etc. may be evaluated. Similarly, agents which mimic cytokines, for example erythropoetin and IL1-17, may be selected, or agents that bind cytokines such as TNF-$\alpha$, before they bind their receptor.

Antigen processing by mononuclear leukocytes (ML) is an important early step in the immune system's ability to recognize and eliminate foreign proteins. Candidate agents can be inserted into ML cell lines and agents selected which alter the intracellular processing of foreign peptides and sequence of the foreign peptide that is presented to T cells by MLs on their cell surface in the context of Class II MHC. One can look for members of the library that enhance immune responses of a particular T cell subset (for example, the peptide would in fact work as a vaccine), or look for a library member that binds more tightly to MHC, thus displacing naturally occurring peptides, but nonetheless the agent would be less immunogenic (less stimulatory to a specific T cell clone). This agent would in fact induce immune tolerance and/or diminish immune responses to foreign proteins. This approach could be used in transplantation, autoimmune diseases, and allergic diseases.

The release of inflammatory mediators (cytokines, leukotrienes, prostaglandins, platelet activating factor, histamine, neuropeptides, and other peptide and lipid mediators) is a key element in maintaining and amplifying aberrant immune responses. Candidate libraries can be inserted into MLs, mast cells, eosinophils, and other cells participating in a specific inflammatory response, and bioactive peptides selected which inhibit the synthesis, release and binding to the cognate receptor of each of these types of mediators.

In a preferred embodiment, the present methods are useful in biotechnology applications. Candidate library expression in mammalian cells can also be considered for other pharmaceutical-related applications, such as modification of protein expression, protein folding, or protein secretion. One such example would be in commercial production of protein pharmaceuticals in CHO or other cells. Candidate libraries resulting in bioactive peptides which select for an increased cell growth rate (perhaps peptides mimicking growth factors or acting as agonists of growth factor signal transduction pathways), for pathogen resistance (see previous section), for lack of sialylation or glycosylation (by blocking glycotransferases or rerouting trafficking of the protein in the cell), for allowing growth on autoclaved media, or for growth in serum free media, would all increase productivity and decrease costs in the production of protein pharmaceuticals.

Random peptides displayed on the surface of circulating cells can be used as tools to identify organ, tissue, and cell specific peptide targeting sequences. Any cell introduced into the bloodstream of an animal expressing a library targeted to the cell surface can be selected for specific organ and tissue targeting. The bioactive peptide sequence identified can then be coupled to an antibody, enzyme, drug, imaging agent or substance for which organ targeting is desired.

Other agents which may be selected using the present invention include: 1) agents which block the activity of transcription factors, using cell lines with reporter genes; 2) agents which block the interaction of two known proteins in cells, using the absence of normal cellular functions, the mammalian two hybrid system or fluorescence resonance energy transfer mechanisms for detection; and 3) agents may be identified by tethering a random peptide to a protein binding region to allow interactions with molecules sterically close, i.e. within a signalling pathway, to localize the effects to a functional area of interest.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLES

Example 1

Selection of Loop Insertion Sites

One example concerns the insertion of sequences of the compostion linker-test sequence-linker into defined sites within engineered GFP loops most likely to tolerate insertions. These loops were selected based on having mobility in the loop or tip of the loop well above that of the most rigid parts of the beta-can structure (Yang et al., Nature Biotechnology 14, 1246–9, 1996; Ormo et al., Science 273, 1392–5, 1996). The loops of most interest are those which are not rigidly coupled to the beta-can structure of the rest of GFP; this lack of rigid coupling may allow the most tolerance for sequence additions within the loops in a library construct. Loops can be selected as those which have the highest temperature factors in the crystal structures, and include loops 130–135, 154–159, 172–175, 188–193, and 208–216 in a GFP monomer. The temperature factor of the loop can be artificially increased by including flexible amino acids such as glycine in the linkers (see below).

The most promising insert sites were selected by removing residues at the termini of the loops whose side chains extended into solution and did not contact either the GFP beta can or other parts of the loops. Loop residues whose side chains bound to other parts of GFP were left unreplaced so as to minimize the likelihood of strong conformational coupling between the random sequences and GFP, which could lead to misfolded protein and/or could diminish the number of fluorescent GFP-fused random peptides by distorting the base of the loop and allowing collisional quenchers access to the fluorophore.

| loop | insert location |
|---|---|
| 1 | replace asp 133 with insert; can't remove glu 132 as carboxylate binds to other residue side chains; this is a very short loop |
| 2 | replace gln 157 and lys 156 with entire insert; lys 156 and gln 157 side chains protrude into solution; lys 158 ion pairs with asp 155 to help close loop so these are generally retained; avoid removing asn 159 as it contacts the main protein body in a number of spots |
| 3 | replace asp 173 with insert, as it is at the outer end of the loop; avoid replacing glu 172 as side chain contacts other side chains in the folded structure; could replace gly 174 too |
| 4 | replace residues 189–192 (gly-asp-gly-pro) with insert; this is not so much a loop as a strand connecting two separated chains; P192, G191, D190 and G189 all protrude into solution and don't appear to form tight contacts with the main protein body; so they appear replaceable |
| 5 | replace asn 212, glu 213 and lys 214 with insert; lys 214 side chain protrudes out into solution; glu 213 helps form the turn as it's side chain binds other side chains in the loop, thus its replacement may cause problems in maintaining a native loop conformation; asn 212 side chain protrudes into solution |

Example 2

Selection of a Test Insert Sequence

To allow a maximal number of different loop inserts or replacements in GFP to fold properly into a fluorescent GFP construct, it may be important to carefully select the linker sequences between the native GFP structure and the inserted sequences making up the actual library inserted into the loop. One way to prevent problems in GFP folding is to conformationally decouple any insert sequence from the GFP structure itself, to minimize local distortions in GFP structure which could either destabilize folding intermediates or could allow access to GFP's buried tripeptide fluorophore of exogenous collisional fluorescence quenchers (Phillips, supra). This can be done by inserting multiple highly flexible amino acid residues between GFP and the library, which impose minimal conformational constraints on the GFP. One or more glycines are ideal for this purpose, as glycine accesses significantly more phi-psi space than even alanine, and is much less restricted than residues with longer side chains (Scheraga, H. A., (1992), "Predicting three-dimensional structures of oligopeptides", in Reviews in Computational Chemstry III, p. 73–142). Thus to optimize the chances of the loop inserts not affecting GFP structure, $-(gly)_n-$ is inserted between these two sequences at each loop containing a library. Minimally n=1, but more optimally $n \geq 2$.

The initial two test inserts were: 1: -GGGGYPYDVPDYASLGGGG- (SEQ ID NO: 52) and 2: -GGGG-YPYD-GGGG- (SEQ ID NO: 53). The first sequence was an 19mer insert (approximately the intended library size) with the influenza hemagglutinin (HA) epitope tag embedded, with glycines added to each end to match the epitope inserted into the dimerizer-folded scaffold, and to add flexibility to the epitope to allow a conformation which binds to polyclonal antisera. This allowed estimation by Western blotting of the expression level of the different constructs. The second insert is truncated to examine the effect on GFP fluorescence of a shorter peptide.

Example 3

Mean Fluorescence of GFP With Test Inserts 1 and 2 in Loops 1–5, Expressed in *E. coli*

The GFP used is EGFP (Clontech Inc., Palo Alto, Calif.) and the two test sequences were inserted at the sites indicated in example 1. An equal number of bacteria (20000) representing clones of a single colonies were analyzed by fluorescence-activated cell sorting on a MoFlo cell sorter (Cytomation Inc., Ft. Collins, Colo.). Intensity of FL1 was averaged. The relative fluorescence intensity was calculated as (WT fluorescence–fluorescence of loop insert)/(WT fluorescence–bkd)×100%. Constructs with insert 1 in loops 1 and 5 were not expressed due to cloning difficulties. Equal amounts of cell lysate from each loop insert were run on a 10% SDS gel and blotted to PVDF. GFP was detected with anti-GFP antibody and the bands were observed using chemiluminescent detection. The intensity of individual bands was measured using a Sharp JX-330 scanning densitomer and Biolmage software. The specific fluorescence was calculated as the ratio of the relative fluorescence to the relative intensity of the Western blot band.

TABLE 1

Mean fluorescence of GFP with different insertion sequences in loops 1–5.

| | relative fluorescence | | relative intensity: Western | | specific fluorescence | |
|---|---|---|---|---|---|---|
| | insert 2 | insert 1 | | | | |
| loop | 12mer | 19mer | insert 2 | insert 1 | insert 2 | insert 1 |
| wild type (no insert) | 1.00 | 1.00 | 1.00 | 1.00 | 1.00 | 1.00 |
| background | 0 | 0 | — | — | — | — |
| 1 | 0 | — | 0.179 | — | 0 | — |

TABLE 1-continued

Mean fluorescence of GFP with different insertion sequences in loops 1–5.

| loop | relative fluorescence | | relative intensity: Western | | specific fluorescence | |
|---|---|---|---|---|---|---|
| | insert 2 12mer | insert 1 19mer | insert 2 | insert 1 | insert 2 | insert 1 |
| 2 | 0.198 | 0.10 | 0.165 | 0.189 | 1.20 | 0.53 |
| 3 | 0.612 | 0.399 | 0.467 | 0.68 | 0.90 | 0.59 |
| 4 | 0.119 | 0.034 | 0.135 | 0.0196 | 6.07 | 1.73 |
| 5 | 0 | — | 0.159 | — | 0 | — | insert 1: -GGGG-YPYDVPDYASL-GGGG (SEQ ID NO: 52)- 2: -GGGG-YPYD-GGGG (SEQ ID NO: 53)-

The results in Table 1 show that in *E. coli*, the defined loop 2, 3 and 4 insertion sites support GFP folding and fluorescence for both the 12mer and 19mer inserts, while inserts in sites 1 and allow expression of GFP without fluorescence for the 12mer insert. Libraries in these sites may thus be useful for screening using other methods for selecting positives than GFP fluorescence. For insertion sites 2, 3 and 4 the fluorescence for a 12mer insert with multiple glycines at each end is at least 10% of that of wild type GFP. The highest fluorescence for the 12mer insert was obtained with insertion in the loop 3 site, while the lowest was obtained from loop 4. This appeared to be due to differing expression levels for each construct, however, as the specific fluorescence was highest for loop 4. For the larger 19mer insert, the highest fluorescence was again obtained with insertion in the loop 3 site, while the lowest was obtained from insertion into the loop 2 site, again due to higher apparent expression levels for the loop 3 insert GFP. Again, the highest specific fluorescence was obtained with loop 4. This suggests that libraries inserted into loop 4, combined with strong promoters to enhance expressed levels of the GFP-library members, will allow screening of these libraries as well as loop 2 and 3 libraries. For the 19mer insert sequence, the loop 2, 3 and 4 inserts all give fluorescence of at least 1% of wild type, and thus should allow screening of libraries in all three loops.

The Western blot results suggest that shorter inserts in loops 1 and 5 allow GFP expression at levels as high or higher than those of loops 2 and 4, albeit without fluorescence. Thus random peptide libraries inserted into these loops can be used to screen cells for phenotypic changes, but the screen for the presence of the library member will have to rely on some property other than GFP fluorescence, such as a readout reflecting a phenotypic change in the cell itself.

Example 4

Mean Fluorescence of GFP With Test Inserts 1 and 2 in Loops 2–4, When Expressed in Jurkat E Cells Insert sequences identical to those shown in example 3 above were used with GFP when expressed in Jurkat E cells. GFP was expressed using the the LTR of the retroviral expression vector, and the Jurkats were infected using Phoenix 293 helper cells. After 48 hours of infection, the Jurkats were subjected to FACS analysis using a Becton-Dickinson FACSCAN cell sorter. For each insert $10^4$ cells were gated using forward-vs. side-scatter selection to isolate live cells. Live cells were selected in a second round using propidium iodide fluorescence, and were then sorted in FL1 on the intensity of their GFP fluorescence. The infection levels of the Jurkat cells with the different constructs were in the range of 30.1%–44.9%, giving on average one peptide construct inserted per cell.

TABLE 2

Geometric mean fluorescence of GFP with different insertion sequences in loops 2–4: Jurkat cells.

| | relative fluorescence | |
|---|---|---|
| loop | insert 2 12mer | insert 1 19mer |
| wild type (no insert) | 1.00 | 1.00 |
| background | 0.000625 | 0.000625 |
| 2 | 0.324 | 0.088 |
| 3 | 1.01 | 0.254 |
| 4 | 0.188 | 0.0625 | insert 1: -GGGG-YPYDVPDYASL-GGGG-
insert 2: -GGGG-YPYD-GGGG-

These results show that the designed insertion sites in loops 2–4 retain a high level of GFP fluorescence when the inserts are flanked by multiple glycines in the tetrapeptide linkers. Thus an insert of 19 residues appears to retain high levels of fluorescence, suggesting that all three loops will allow insertion of random peptide libraries and their screening. Such screening should require only a level of fluorescence distinguishable from background, or one decade up in FL1.

The successful observation of fluorescence of nearly 10% or more of wild type in GFP with both sequences in the loop 2 insertion site was not seen by Abedi et al. (1998) and suggests that inclusion of the glycine linkers on either side of the insert sequence, combined with excision of residues at the tip of the loop, may make this loop a unique and useful site for insertion of random library sequences. The high levels of relative fluorescence for inserts 1 and 2 in loops 2–4 suggest that the tetraglycine linkers will allow successful insertion of random peptide libraries into these particular sites; shorter libraries may be preferred.

Example 5

Mean Fluorescence of GFP With Test Inserts 1 and 2 in Loops 2–4, When Expressed in Phoenix 293 Cells Insert sequences identical to those shown in example 3 above were used with GFP when expressed in Phoenix 293 cells. GFP was expressed using the 96.7 CMV-promoter driven CRU-5 retroviral expression vector in transfected Phoenix 293 cells. The transfection efficiency was 40–45%. After 48 hours of transfection, the Jurkats were subjected to FACS analysis using a Becton-Dickinson FACSCAN cell sorter. For each insert approximately $10^4$ cells were gated using forward-vs. side-scatter selection to isolate live cells. Live cells were selected in a second round using propidium iodide fluorescence, and were then sorted in FL1 on the intensity of their GFP fluorescence. The transfection efficiency for all constructs reported was in the range of 24–42%, giving on average one plasmid/cell expressing the GFP construct.

TABLE 3

Geometric mean fluorescence of GFP with different insertion sequences in loops 2–4: Phoenix 293 cells.

| | relative fluorescence | | relative intensity: Western | | specific fluorescence | |
|---|---|---|---|---|---|---|
| | insert 2 | insert 1 | | | | |
| loop | 12mer | 19mer | insert 2 | insert 1 | insert 2 | insert 1 |
| wild type (no insert) | 1.00 ± .078 | 1.00 ± .078 | 1.00 | 1.00 | 1.00 | 1.00 |
| background | 0.00 | 0.00 | 0 | 0 | | |
| 2 | 1.07 ± 18* | 0.676 ± .078 | 0.44 | 0.40 | 2.43 | 1.71 |
| 3 | 1.32 ± 12* | 0.471 ± .055 | 0.69 | 0.99 | 1.91 | 0.538 |
| 4 | 0.51 ± .08 | 0.422 ± .071 | 0.36 | 0.19 | 3.89 | 2.22 | insert 1: -GGGG-YPYDVPDYASL-GGGG (SEQ ID NO: 52)- 2: -GGGG-YPYD-GGGG (SEQ ID NO: 53)-

The numbers for the relative fluorescence of the loop 2, 3, and 4 inserts are derived from the average value ±1 standard deviation for 1–2 independent clones with the specified insert. The specific fluorescence is the ratio of the relative fluorescence to the Western blot relative intensity. The standard deviation of the relative fluorescence was calculated as [fluorescence of insert/fluorescence of WT {(std. dev of insert fluorescence/insert fluorescence)$^2$+(std. dev. of WT fluorescence/WT fluorescence)$^2$}]$^{0.6}$(Bevington, P. 1969. Data reduction and error analysis for the physical sciences. New York: McGraw Hill, p. 61–2). Data with an asterisk* was derived from cells with a 60–70% transfection efficiency and so can only be qualitatively compared with the rest of the data.

These results for 293 cells show that in these cells the designed insertion sites in loops 2–4 retain a very high level of GFP fluorescence when the inserts are flanked by multiple glycines in the tetrapeptide linkers, in some cases higher than wild type GFP fluorescence. Thus both inserts of 19 and 12 residues retain high levels of fluorescence, suggesting that all three loops will allow insertion of random peptide libraries and their screening, and that libraries in all three loops are roughly equivalent. The high level of relative fluorescence of loop 3 appears to be mainly due to a higher expression level than the GFP construct with inserts in loops 1 and 2, although the expression levels of all 3 loop-inserts are at least 19% of the wild type GFP levels. Since the specific fluorescence of both inserts in loops 2 and 4 is greater than the insert in loop 3, a higher level of expression could compensate for the overall lower level of fluorescence of these loop 2 and 4 inserts. Since expression of these constructs is with a stronger promoter than expression in *E. coli* or Jurkat cells, this also suggests that use of stronger promoters than the retroviral LTR or promoter in *E. coli* will make more loop insertion sites usable for screens.

We claim:

1. A library of fusion nucleic acids wherein each fusion nucleic acid comprises:

a) nucleic acid encoding a random peptide; and b) nucleic acid encoding green fluorescent protein (GFP); wherein said nucleic acid encoding a random peptide is inserted internally into a nucleic acid encoding GFP, wherein a nucleic acid encoding at least one of the amino acids of GFP selected from the group of amino acids at positions 130–135, 154–159, 172–175, 188–193, and 208–216 is replaced by said nucleic acid encoding a random peptide.

2. A library of retroviral vectors comprising the library of fusion nucleic acids according to claim 1.

3. A library of host cells comprising the library of retroviral vectors of according to claim 2.

4. A library of host cells comprising the library of fusion nucleic acids according to claim 1.

5. A library of host cells according to claim 4, wherein said host cells are mammalian host cells.

6. A library of fusion nucleic acids according to claim 1, wherein said nucleic acid encoding a random peptide is inserted into the nucleic acid encoding GFP within positions encoding amino acids 130 to 135.

7. A library of fusion nucleic acids according to claim 1, wherein said nucleic acid encoding said random peptide is inserted into the nucleic acid encoding GFP within positions encoding amino acids 154 to 159.

8. A library of fusion nucleic acids according to claim 1, wherein said nucleic acid encoding said random peptide is inserted into the nucleic acid encoding GFP within positions encoding amino acids 172 to 175.

9. A library of fusion nucleic acids according to claim 1, wherein said nucleic acid encoding said random peptide is inserted into the nucleic acid encoding GFP within positions encoding amino acids 188 to 193.

10. A library of fusion nucleic acids according to claim 1, wherein said nucleic acid encoding said random peptide is inserted into the nucleic acid encoding GFP within positions encoding amino acids 208 to 216.

11. A library of fusion nucleic acids according to claim 1, wherein said nucleic acid encoding a random peptide replaces at least three nucleotides of the nucleic acid encoding GFP.

12. A library of fusion nucleic acids according to claim 1, wherein each fusion nucleic acid further comprises:

c) nucleic acid encoding at least one fusion partner.

13. A library of fusion nucleic acids according to claim 12, wherein said fusion partner is a presentation structure which presents said peptide in a conformationally restricted form.

14. A library of fusion nucleic acids according to claim 13, wherein said presentation structure is a dimerizing sequence.

15. A library of fusion nucleic acids according to claim 12, wherein said fusion partner is a linker.

16. A library of nucleic acids according to claim 15, wherein said linker comprises -(gly)$_n$-, wherein n≧2.

17. A library of fusion nucleic acids according to claim 12, wherein each fusion nucleic acid comprises sequences encoding:

i) a first linker between the N-terminus of said random peptide and said GFP; and ii) a second linker between the C-terminus of said random peptide and said GFP.

18. A library of fusion nucleic acids according to claim 1, wherein said sequence encoding at least one of the amino acids of GFP is selected from the group of amino acids at positions 130–135, 154–159, 172–175, 188–193, and 208–216.

19. A method of screening for bioactive peptides conferring a particular phenotype comprising:

a) providing a library of cells containing a library of fusion nucleic acids wherein each fusion nucleic acid encodes a fusion protein comprising:
      i) GFP; and
      ii) a random peptide;
      wherein said random peptide is inserted in an internal position of the GFP and wherein a nucleic acid encoding at least one of the amino acids of GFP is replaced by said nucleic acid encoding a random peptide;

b) providing conditions under which said fusion protein is expressed; and c) assaying said cells for said phenotype.

20. A method according to claim 1, wherein said providing is accomplished by transfecting said cells with a library of retroviral vectors comprising said library of fusion nucleic acids.

21. A method according to claim 19, wherein said sequence encoding at least one of the amino acids of GFP is selected from the group of amino acids at positions 130–135, 154–159, 172–175, 188–193, and 208–216.

* * * * *

SEQUENCE LISTING

<160> NUMBER OF SEQ ID NOS: 55

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: synthetic

<400> SEQUENCE: 1

Leu Glu Glu Phe Gly Ser
 1               5

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: synthetic

<400> SEQUENCE: 2

Tyr Pro Tyr Asp Val Pro Asp Tyr Ala Ser Leu
 1               5                  10

<210> SEQ ID NO 3

```
<211> LENGTH: 9
<212> TYPE: PRT
<213> ORGANISM: Artificial Sequence
<220> FEATURE:
<221> NAME/KEY: UNSURE
<222> LOCATION: (1)..(3)
<223> OTHER INFORMATION: The x at positions 1, 2 and 3 represents a
      randomized residue.
<221> NAME/KEY: UNSURE
<222> LOCATION: (6)
<223> OTHER INFORMATION: The x at position 6 represents a randomized
      residue.
<221> NAME/KEY: UNSURE
<222> LOCATION: (8)..(9)
<223> OTHER INFORMATION: The x at positions 8 and 9 represents a
      randomized residue.
<223> OTHER INFORMATION: Description of Artificial Sequence:  synthetic

<400> SEQUENCE: 3

Xaa Xaa Xaa Pro Pro Xaa Pro Xaa Xaa
 1               5

<210> SEQ ID NO 4
<211> LENGTH: 61
<212> TYPE: PRT
<213> ORGANISM: Artificial Sequence
<220> FEATURE:
<223> OTHER INFORMATION: Description of Artificial Sequence:  synthetic
<300> PUBLICATION INFORMATION:
<303> JOURNAL: EMBO J.
<304> VOLUME: 13
<305> ISSUE: 22
<306> PAGES: 5303-5309
<307> DATE: 1994

<400> SEQUENCE: 4

Met Gly Cys Ala Ala Leu Glu Ser Glu Val Ser Ala Leu Glu Ser Glu
 1               5                  10                  15

Val Ala Ser Leu Glu Ser Glu Val Ala Ala Leu Gly Arg Gly Asp Met
                 20                  25                  30

Pro Leu Ala Ala Val Lys Ser Lys Leu Ser Ala Val Lys Ser Lys Leu
             35                  40                  45

Ala Ser Val Lys Ser Lys Leu Ala Ala Cys Gly Pro Pro
         50                  55                  60

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence:  synthetic

<400> SEQUENCE: 5

Gly Arg Gly Asp Met Pro
 1               5

<210> SEQ ID NO 6
<211> LENGTH: 69
<212> TYPE: PRT
<213> ORGANISM: Artificial Sequence
<220> FEATURE:
<223> OTHER INFORMATION: Description of Artificial Sequence:  synthetic

<400> SEQUENCE: 6

Met Gly Arg Asn Ser Gln Ala Thr Ser Gly Phe Thr Phe Ser His Phe
 1               5                  10                  15

Tyr Met Glu Trp Val Arg Gly Gly Glu Tyr Ile Ala Ala Ser Arg His
                 20                  25                  30
```

-continued

```
Lys His Asn Lys Tyr Thr Thr Glu Tyr Ser Ala Ser Val Lys Gly Arg
            35                  40                  45

Tyr Ile Val Ser Arg Asp Thr Ser Gln Ser Ile Leu Tyr Leu Gln Lys
        50                  55                  60

Lys Lys Gly Pro Pro
 65

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: synthetic

<400> SEQUENCE: 7

Phe Gln Cys Glu Glu Cys
  1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: synthetic

<400> SEQUENCE: 8

His Ile Arg Ser His Thr Gly
  1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: synthetic

<400> SEQUENCE: 9

Val Lys Cys Phe Asn Cys
  1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: synthetic

<400> SEQUENCE: 10

His Thr Ala Arg Asn Cys Arg
  1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: synthetic

<400> SEQUENCE: 11

Met Asn Pro Asn Cys Ala Arg Cys Gly
  1               5

<210> SEQ ID NO 12
<211> LENGTH: 5
<212> TYPE: PRT
```

```
<213> ORGANISM: Artificial Sequence
<220> FEATURE:
<223> OTHER INFORMATION: Description of Artificial Sequence: synthetic

<400> SEQUENCE: 12

His Lys Ala Cys Phe
  1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: synthetic

<400> SEQUENCE: 13

Glu Phe Leu Ile Val Lys Ser
  1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: synthetic

<400> SEQUENCE: 14

Glu Glu Phe Leu Ile Val Lys Lys Ser
  1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: synthetic

<400> SEQUENCE: 15

Phe Glu Ser Ile Lys Leu Val
  1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: synthetic

<400> SEQUENCE: 16

Val Ser Ile Lys Phe Glu Leu
  1               5

<210> SEQ ID NO 17
<211> LENGTH: 7
<212> TYPE: PRT
<213> ORGANISM: Monkey virus
<300> PUBLICATION INFORMATION:
<303> JOURNAL: Cell
<305> ISSUE: 39
<306> PAGES: 499-509
<307> DATE: 1984

<400> SEQUENCE: 17

Pro Lys Lys Lys Arg Lys Val
  1               5

<210> SEQ ID NO 18
```

```
<211> LENGTH: 6
<212> TYPE: PRT
<213> ORGANISM: Homo sapiens

<400> SEQUENCE: 18

Ala Arg Arg Arg Arg Pro
 1               5

<210> SEQ ID NO 19
<211> LENGTH: 10
<212> TYPE: PRT
<213> ORGANISM: Homo sapiens
<300> PUBLICATION INFORMATION:
<303> JOURNAL: Cell
<305> ISSUE: 64
<306> PAGES: 961-
<307> DATE: 1990

<400> SEQUENCE: 19

Glu Glu Val Gln Arg Lys Arg Gln Lys Leu
 1               5                  10

<210> SEQ ID NO 20
<211> LENGTH: 9
<212> TYPE: PRT
<213> ORGANISM: Homo sapiens
<300> PUBLICATION INFORMATION:
<303> JOURNAL: Cell
<305> ISSUE: 64
<306> PAGES: 961-
<307> DATE: 1991

<400> SEQUENCE: 20

Glu Glu Lys Arg Lys Arg Thr Tyr Glu
 1               5

<210> SEQ ID NO 21
<211> LENGTH: 20
<212> TYPE: PRT
<213> ORGANISM: Xenopus
<300> PUBLICATION INFORMATION:
<303> JOURNAL: Cell
<305> ISSUE: 30
<306> PAGES: 449-458
<307> DATE: 1982
<300> PUBLICATION INFORMATION:
<303> JOURNAL: J. Cell Biol.
<305> ISSUE: 30
<306> PAGES: 449-458
<307> DATE: 1988

<400> SEQUENCE: 21

Ala Val Lys Arg Pro Ala Ala Thr Lys Lys Ala Gly Gln Ala Lys Lys
 1               5                  10                  15

Lys Lys Leu Asp
            20

<210> SEQ ID NO 22
<211> LENGTH: 31
<212> TYPE: PRT
<213> ORGANISM: Artificial Sequence
<220> FEATURE:
<223> OTHER INFORMATION: Description of Artificial Sequence:   synthetic
<300> PUBLICATION INFORMATION:
<303> JOURNAL: Proc. Natl. Acad. Sci. U.S.A.
<305> ISSUE: 82
<306> PAGES: 5126-
<307> DATE: 1985

<400> SEQUENCE: 22
```

-continued

Met Ala Ser Pro Leu Thr Arg Phe Leu Ser Leu Asn Leu Leu Leu Leu
 1               5                  10                  15

Gly Glu Ser Ile Leu Gly Ser Gly Glu Ala Lys Pro Gln Ala Pro
                20                  25                  30

<210> SEQ ID NO 23
<211> LENGTH: 21
<212> TYPE: PRT
<213> ORGANISM: Homo sapiens
<300> PUBLICATION INFORMATION:
<303> JOURNAL: Nature
<305> ISSUE: 339
<306> PAGES: 61-
<307> DATE: 1989

<400> SEQUENCE: 23

Met Ser Ser Phe Gly Tyr Arg Thr Leu Thr Val Ala Leu Phe Thr Leu
 1               5                  10                  15

Ile Cys Cys Pro Gly
                20

<210> SEQ ID NO 24
<211> LENGTH: 51
<212> TYPE: PRT
<213> ORGANISM: Mouse
<300> PUBLICATION INFORMATION:
<303> JOURNAL: Proc. Natl. Acad. Sci. U.S.A.
<305> ISSUE: 82
<306> PAGES: 5126-
<307> DATE: 1985

<400> SEQUENCE: 24

Pro Gln Arg Pro Glu Asp Cys Arg Pro Arg Gly Ser Val Lys Gly Thr
 1               5                  10                  15

Gly Leu Asp Phe Ala Cys Asp Ile Tyr Ile Trp Ala Pro Leu Ala Gly
                20                  25                  30

Ile Cys Val Ala Leu Leu Leu Ser Leu Ile Ile Thr Leu Ile Cys Tyr
            35                  40                  45

His Ser Arg
        50

<210> SEQ ID NO 25
<211> LENGTH: 33
<212> TYPE: PRT
<213> ORGANISM: Homo sapiens
<300> PUBLICATION INFORMATION:
<303> JOURNAL: Nature
<305> ISSUE: 339
<306> PAGES: 61-
<307> DATE: 1989

<400> SEQUENCE: 25

Met Val Ile Ile Val Thr Val Val Ser Val Leu Leu Ser Leu Phe Val
 1               5                  10                  15

Thr Ser Val Leu Leu Cys Phe Ile Phe Gly Gln His Leu Arg Gln Gln
                20                  25                  30

Arg

<210> SEQ ID NO 26
<211> LENGTH: 36
<212> TYPE: PRT
<213> ORGANISM: Artificial Sequence
<220> FEATURE:
<223> OTHER INFORMATION: Description of Artificial Sequence: synthetic

```
<300> PUBLICATION INFORMATION:
<303> JOURNAL: Nature
<304> VOLUME: 333
<305> ISSUE: 6170
<306> PAGES: 269-272
<307> DATE: 1988
<300> PUBLICATION INFORMATION:
<303> JOURNAL: J. Biol. Chem.
<305> ISSUE: 266
<306> PAGES: 1250-
<307> DATE: 1991

<400> SEQUENCE: 26

Pro Asn Lys Gly Ser Gly Thr Thr Ser Gly Thr Thr Arg Leu Leu Ser
 1               5                  10                  15

Gly His Thr Cys Phe Thr Leu Thr Gly Leu Leu Gly Val Thr Met
            20                  25                  30

Gly Leu Leu Thr
         35

<210> SEQ ID NO 27
<211> LENGTH: 14
<212> TYPE: PRT
<213> ORGANISM: Chicken
<300> PUBLICATION INFORMATION:
<303> JOURNAL: Mol. Cell. Biol.
<304> VOLUME: 4
<305> ISSUE: 9
<306> PAGES: 1834-
<307> DATE: 1984
<300> PUBLICATION INFORMATION:
<303> JOURNAL: Science
<305> ISSUE: 262
<306> PAGES: 1019-1024
<307> DATE: 1993

<400> SEQUENCE: 27

Met Gly Ser Ser Lys Ser Lys Pro Lys Asp Pro Ser Gln Arg
 1               5                  10

<210> SEQ ID NO 28
<211> LENGTH: 26
<212> TYPE: PRT
<213> ORGANISM: Artificial Sequence
<220> FEATURE:
<223> OTHER INFORMATION: Description of Artificial Sequence:  synthetic
<300> PUBLICATION INFORMATION:
<303> JOURNAL: J. Biol. Chem.
<305> ISSUE: 269
<306> PAGES: 27791-
<307> DATE: 1994

<400> SEQUENCE: 28

Leu Leu Gln Arg Leu Phe Ser Arg Gln Asp Cys Cys Gly Asn Cys Ser
 1               5                  10                  15

Asp Ser Glu Glu Glu Leu Pro Thr Arg Leu
            20                  25

<210> SEQ ID NO 29
<211> LENGTH: 19
<212> TYPE: PRT
<213> ORGANISM: Artificial Sequence
<220> FEATURE:
<223> OTHER INFORMATION: Description of Artificial Sequence:  synthetic
<300> PUBLICATION INFORMATION:
<303> JOURNAL: J. Mol. Neurosci.
<304> VOLUME: 5
<305> ISSUE: 3
<306> PAGES: 207-
<307> DATE: 1994
```

```
<400> SEQUENCE: 29

Lys Gln Phe Arg Asn Cys Met Thr Ser Leu Cys Cys Gly Lys Asn Pro
  1               5                  10                  15

Leu Gly Asp

<210> SEQ ID NO 30
<211> LENGTH: 19
<212> TYPE: PRT
<213> ORGANISM: Artificial Sequence
<220> FEATURE:
<223> OTHER INFORMATION: Description of Artificial Sequence:  synthetic
<300> PUBLICATION INFORMATION:
<303> JOURNAL: Nature
<305> ISSUE: 302
<306> PAGES: 33-
<307> DATE: 1983

<400> SEQUENCE: 30

Leu Asn Pro Pro Asp Glu Ser Gly Pro Gly Cys Met Ser Cys Lys Cys
  1               5                  10                  15

Val Leu Ser

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence:  synthetic
<300> PUBLICATION INFORMATION:
<303> JOURNAL: Ann. N. Y. Acad. Sci.
<305> ISSUE: 674
<306> PAGES: 58-
<307> DATE: 1992

<400> SEQUENCE: 31

Lys Phe Glu Arg Gln
  1               5

<210> SEQ ID NO 32
<211> LENGTH: 36
<212> TYPE: PRT
<213> ORGANISM: Artificial Sequence
<220> FEATURE:
<223> OTHER INFORMATION: Description of Artificial Sequence:  synthetic
<300> PUBLICATION INFORMATION:
<303> JOURNAL: Cell. Mol. Biol. Res.
<305> ISSUE: 41
<306> PAGES: 405-
<307> DATE: 1995

<400> SEQUENCE: 32

Met Leu Ile Pro Ile Ala Gly Phe Phe Ala Leu Ala Gly Leu Val Leu
  1               5                  10                  15

Ile Val Leu Ile Ala Tyr Leu Ile Gly Arg Lys Arg Ser His Ala Gly
                 20                  25                  30

Tyr Gln Thr Ile
         35

<210> SEQ ID NO 33
<211> LENGTH: 35
<212> TYPE: PRT
<213> ORGANISM: Homo sapiens
<300> PUBLICATION INFORMATION:
<303> JOURNAL: Biochem. Biophys. Res. Commun.
<305> ISSUE: 205
<306> PAGES: 1-5
```

-continued

```
<307> DATE: 1994

<400> SEQUENCE: 33

Leu Val Pro Ile Ala Val Gly Ala Ala Leu Ala Gly Val Leu Ile Leu
 1               5                  10                  15

Val Leu Leu Ala Tyr Phe Ile Gly Leu Lys His His His Ala Gly Tyr
            20                  25                  30

Glu Gln Phe
        35

<210> SEQ ID NO 34
<211> LENGTH: 27
<212> TYPE: PRT
<213> ORGANISM: Yeast
<300> PUBLICATION INFORMATION:
<303> JOURNAL: Eur. J. Biochem.
<305> ISSUE: 165
<306> PAGES: 1-6
<307> DATE: 1987

<400> SEQUENCE: 34

Met Leu Arg Thr Ser Ser Leu Phe Thr Arg Arg Val Gln Pro Ser Leu
 1               5                  10                  15

Phe Ser Arg Asn Ile Leu Arg Leu Gln Ser Thr
            20                  25

<210> SEQ ID NO 35
<211> LENGTH: 25
<212> TYPE: PRT
<213> ORGANISM: Yeast
<300> PUBLICATION INFORMATION:
<303> JOURNAL: Eur. J. Biochem.
<305> ISSUE: 165
<306> PAGES: 1-6
<307> DATE: 1987

<400> SEQUENCE: 35

Met Leu Ser Leu Arg Gln Ser Ile Arg Phe Phe Lys Pro Ala Thr Arg
 1               5                  10                  15

Thr Leu Cys Ser Ser Arg Tyr Leu Leu
            20                  25

<210> SEQ ID NO 36
<211> LENGTH: 64
<212> TYPE: PRT
<213> ORGANISM: Yeast
<300> PUBLICATION INFORMATION:
<303> JOURNAL: Eur. J. Biochem.
<305> ISSUE: 165
<306> PAGES: 1-6
<307> DATE: 1987

<400> SEQUENCE: 36

Met Phe Ser Met Leu Ser Lys Arg Trp Ala Gln Arg Thr Leu Ser Lys
 1               5                  10                  15

Ser Phe Tyr Ser Thr Ala Thr Gly Ala Ala Ser Lys Ser Gly Lys Leu
            20                  25                  30

Thr Gln Lys Leu Val Thr Ala Gly Val Ala Ala Ala Gly Ile Thr Ala
        35                  40                  45

Ser Thr Leu Leu Tyr Ala Asp Ser Leu Thr Ala Glu Ala Met Thr Ala
     50                  55                  60

<210> SEQ ID NO 37
<211> LENGTH: 41
```

```
<212> TYPE: PRT
<213> ORGANISM: Yeast
<300> PUBLICATION INFORMATION:
<303> JOURNAL: Eur. J. Biochem.
<305> ISSUE: 165
<306> PAGES: 1-6
<307> DATE: 1987

<400> SEQUENCE: 37

Met Lys Ser Phe Ile Thr Arg Asn Lys Thr Ala Ile Leu Ala Thr Val
 1               5                  10                  15

Ala Ala Thr Gly Thr Ala Ile Gly Ala Tyr Tyr Tyr Tyr Asn Gln Leu
             20                  25                  30

Gln Gln Gln Gln Gln Arg Gly Lys Lys
         35                  40

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence:  synthetic
<300> PUBLICATION INFORMATION:
<303> JOURNAL: Royal Society London Transaction B
<306> PAGES: 1-10

<400> SEQUENCE: 38

Lys Asp Glu Leu
 1

<210> SEQ ID NO 39
<211> LENGTH: 15
<212> TYPE: PRT
<213> ORGANISM: Adenovirus
<300> PUBLICATION INFORMATION:
<303> JOURNAL: EMBO J.
<305> ISSUE: 9
<306> PAGES: 3153-
<307> DATE: 1990

<400> SEQUENCE: 39

Leu Tyr Leu Ser Arg Arg Ser Phe Ile Asp Glu Lys Lys Met Pro
 1               5                  10                  15

<210> SEQ ID NO 40
<211> LENGTH: 19
<212> TYPE: PRT
<213> ORGANISM: Artificial Sequence
<220> FEATURE:
<223> OTHER INFORMATION: Description of Artificial Sequence:  synthetic

<400> SEQUENCE: 40

Leu Asn Pro Pro Asp Glu Ser Gly Pro Gly Cys Met Ser Cys Lys Cys
 1               5                  10                  15

Val Leu Ser

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence:  synthetic
<300> PUBLICATION INFORMATION:
<303> JOURNAL: Proc. Natl. Acad. Sci. U.S.A.
<305> ISSUE: 91
<306> PAGES: 11963-
<307> DATE: 1994
```

```
<400> SEQUENCE: 41

Leu Thr Glu Pro Thr Gln Pro Thr Arg Asn Gln Cys Cys Ser Asn
  1               5                  10                  15

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence:  synthetic
<300> PUBLICATION INFORMATION:
<303> JOURNAL: EMBO J.
<305> ISSUE: 1
<306> PAGES: 3053-
<307> DATE: 1996

<400> SEQUENCE: 42

Arg Thr Ala Leu Gly Asp Ile Gly Asn
  1               5

<210> SEQ ID NO 43
<211> LENGTH: 21
<212> TYPE: PRT
<213> ORGANISM: Artificial Sequence
<220> FEATURE:
<223> OTHER INFORMATION: Description of Artificial Sequence:  synthetic
<300> PUBLICATION INFORMATION:
<303> JOURNAL: J. Immunol.
<305> ISSUE: 155
<306> PAGES: 3946-
<307> DATE: 1995

<400> SEQUENCE: 43

Met Tyr Arg Met Gln Leu Leu Ser Cys Ile Ala Leu Ser Leu Ala Ala
  1               5                  10                  15

Leu Val Thr Asn Ser
              20

<210> SEQ ID NO 44
<211> LENGTH: 29
<212> TYPE: PRT
<213> ORGANISM: Artificial Sequence
<220> FEATURE:
<223> OTHER INFORMATION: Description of Artificial Sequence:  synthetic
<300> PUBLICATION INFORMATION:
<303> JOURNAL: Nucleic Acids Res.
<305> ISSUE: 7
<306> PAGES: 30-
<307> DATE: 1979

<400> SEQUENCE: 44

Met Ala Thr Gly Ser Arg Thr Ser Leu Leu Leu Ala Phe Gly Leu Leu
  1               5                  10                  15

Cys Leu Pro Trp Leu Gln Glu Gly Ser Ala Phe Pro Thr
              20                  25

<210> SEQ ID NO 45
<211> LENGTH: 27
<212> TYPE: PRT
<213> ORGANISM: Preproinsulin
<300> PUBLICATION INFORMATION:
<303> JOURNAL: Nature
<305> ISSUE: 284
<306> PAGES: 26-
<307> DATE: 1980

<400> SEQUENCE: 45
```

```
Met Ala Leu Trp Met Arg Leu Leu Pro Leu Leu Ala Leu Leu Ala Leu
 1               5                  10                  15

Trp Gly Pro Asp Pro Ala Ala Ala Phe Val Asn
             20                  25
```

<210> SEQ ID NO 46
<211> LENGTH: 18
<212> TYPE: PRT
<213> ORGANISM: Influenza virus
<300> PUBLICATION INFORMATION:
<303> JOURNAL: Proc. Natl. Acad. Sci. U.S.A.
<305> ISSUE: 80
<306> PAGES: 3563-

<400> SEQUENCE: 46

```
Met Lys Ala Lys Leu Leu Val Leu Leu Tyr Ala Phe Val Ala Gly Asp
 1               5                  10                  15

Gln Ile
```

<210> SEQ ID NO 47
<211> LENGTH: 24
<212> TYPE: PRT
<213> ORGANISM: Artificial Sequence
<220> FEATURE:
<223> OTHER INFORMATION: Description of Artificial Sequence: synthetic

<400> SEQUENCE: 47

```
Met Gly Leu Thr Ser Gln Leu Leu Pro Pro Leu Phe Phe Leu Leu Ala
 1               5                  10                  15

Cys Ala Gly Asn Phe Val His Gly
             20
```

<210> SEQ ID NO 48
<211> LENGTH: 10
<212> TYPE: PRT
<213> ORGANISM: Artificial Sequence
<220> FEATURE:
<221> NAME/KEY: UNSURE
<222> LOCATION: (3)..(6)
<223> OTHER INFORMATION: The x at positions 3, 4, 5 and 6 represents any
      amino acid.
<223> OTHER INFORMATION: Description of Artificial Sequence: synthetic

<400> SEQUENCE: 48

```
Met Gly Xaa Xaa Xaa Xaa Gly Gly Pro Pro
 1               5                  10
```

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: synthetic

<400> SEQUENCE: 49

```
Gly Ser Gly Gly Ser
 1               5
```

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence: synthetic

<400> SEQUENCE: 50

Gly Gly Gly Ser
1

<210> SEQ ID NO 51
<211> LENGTH: 12
<212> TYPE: PRT
<213> ORGANISM: Artificial Sequence
<220> FEATURE:
<221> NAME/KEY: UNSURE
<222> LOCATION: (2)..(11)
<223> OTHER INFORMATION: The x at positions 2, 3, 4, 5, 6, 7, 8, 9, 10
      and 11 represents randome cyclized peptide.
<223> OTHER INFORMATION: Description of Artificial Sequence: synthetic

<400> SEQUENCE: 51

Cys Xaa Xaa Xaa Xaa Xaa Xaa Xaa Xaa Xaa Xaa Cys
1               5                   10

<210> SEQ ID NO 52
<211> LENGTH: 19
<212> TYPE: PRT
<213> ORGANISM: Artificial Sequence
<220> FEATURE:
<223> OTHER INFORMATION: Description of Artificial Sequence: synthetic

<400> SEQUENCE: 52

Gly Gly Gly Gly Tyr Pro Tyr Asp Val Pro Asp Tyr Ala Ser Leu Gly
1               5                   10                  15

Gly Gly Gly

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 53

Gly Gly Gly Gly Tyr Pro Tyr Asp Gly Gly Gly Gly
1               5                   10

<210> SEQ ID NO 54
<211> LENGTH: 60
<212> TYPE: DNA
<213> ORGANISM: Artificial Sequence
<220> FEATURE:
<221> NAME/KEY: CDS
<222> LOCATION: (1)..(60)
<223> OTHER INFORMATION: Description of Artificial Sequence: synthetic

<400> SEQUENCE: 54 atg ggc nnk nnk nnk nnk nnk aga cct ctg cct cca sbk cct sbk sbk        48
Met Gly Xaa Xaa Xaa Xaa Xaa Arg Pro Leu Pro Pro Xaa Pro Xaa Xaa
1               5                   10                  15 gga ggc cca cct                                                        60
Gly Gly Pro Pro
            20

<210> SEQ ID NO 55
<211> LENGTH: 20
<212> TYPE: PRT
<213> ORGANISM: Artificial Sequence
<220> FEATURE:
<223> OTHER INFORMATION: :

-continued

<400> SEQUENCE: 55

Met Gly Xaa Xaa Xaa Xaa Xaa Arg Pro Leu Pro Pro Xaa Pro Xaa Xaa
1               5                   10                  15

Gly Gly Pro Pro
            20